US007399585B2

(12) United States Patent
Gau

(10) Patent No.: US 7,399,585 B2
(45) Date of Patent: Jul. 15, 2008

(54) BIOLOGICAL IDENTIFICATION SYSTEM WITH INTEGRATED SENSOR CHIP

(75) Inventor: Vincent Jen-Jr. Gau, Los Angeles, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/848,727

(22) Filed: May 3, 2001

(65) Prior Publication Data

US 2002/0123048 A1    Sep. 5, 2002

Related U.S. Application Data

(60) Provisional application No. 60/201,603, filed on May 3, 2000.

(51) Int. Cl.
C12Q 1/68 (2006.01)
(52) U.S. Cl. .............................................. 435/6; 506/3
(58) Field of Classification Search ................ 435/4, 435/7.1, 287.1, 287.2, 287.8; 436/149, 150
See application file for complete search history.

(56) References Cited

U.S. PATENT DOCUMENTS

| | | | | | |
|---|---|---|---|---|---|
| 4,963,245 | A | * | 10/1990 | Weetall | 205/777.5 |
| 5,120,421 | A | * | 6/1992 | Glass et al. | 204/406 |
| 5,200,051 | A | * | 4/1993 | Cozzette et al. | 204/403.07 |
| 5,403,700 | A | * | 4/1995 | Heller et al. | 430/311 |
| 5,567,302 | A | * | 10/1996 | Song et al. | 205/777.5 |
| 5,632,957 | A | * | 5/1997 | Heller et al. | 422/68.1 |
| 6,238,624 | B1 | * | 5/2001 | Heller et al. | 422/68.1 |
| 6,268,161 | B1 | * | 7/2001 | Han et al. | 435/14 |
| 6,294,062 | B1 | * | 9/2001 | Buck et al. | 204/400 |
| 6,518,024 | B2 | * | 2/2003 | Choong et al. | 435/6 |

OTHER PUBLICATIONS

Webster's II New Riverside University Dictionary, 1994, Houghton Mifflin Comapny, p. 920.*
Electrochemistry Dictionary, Oct. 3, 2005, website at http://electrochem.cwru.edu/ed/dict.htm, for the terms: "potential" and "electrical potential".*
Wink et. al., "Self-assembled Monolayers for Biosensors", 1997, The Analyst, vol. 122, Issues 4, pp. 43R-50R.*
Spinke et al., "Molecular recognition at self-assembled monolayers: the construction of multicomponent multilayers", Jul. 1993, Langmuir, vol. 9, No. 7, pp. 1821-1825.*
Abbott, N.L.; Gorman, C.B.; Whitesides, G.M., "Active Control of Wetting Using Applied Electrical Potentials and Self-Assembled Monolayers" Langmuir, 11, Issue 1, Jan. 1995, 16-18.
Abbott, N.L.; Rolison, D.R.: Whitesides, G.M., "Combining Micromachining And Molecular Self-Assembly To Fabricate Microelectrodes" Langmuir, 10, Issue 8, Aug. 1994, 2672-2682.

Abdel-Hamid, I. Ivnitski, D., Atanasov, P., Wilkins, E., "Fast Amperometric Assay for *E. coli* 0157:H7 Using Partially Immersed Immunoelectrodes", Electroanalysis 1998, 10(11), 758-763.
Abdel-Hamid, I.; Ivnitski, D.; Atanasov, P.; Wilkins, E.; "Flow-through immunofiltration assay system for rapid detection of *E. coli* 0157:H7", Biosensors & Bioelectronics 14 (1999), 309-316.
Andrade, J.D., "Surface and Interface Aspects of Biomedical Polymers: Protein Adsorption" Plenum, New York, 1985.
Bain, C: ; Troughton, E.; Tao, Y.; Evall, J.; Whitesides, G.; Nuzzo, R.; "Formation of Monolayer Films by the Spontaneous Assembly of Organic Thiols from Solution onto Gold," American Chemical Society, 1989, 111, 321.
Baxter, Ian; Cother, Lisa D.; Dupuy, Carole; Lickiss, Paul D.; White, Andrew J.P.; Williams, David J.; "Hydrogen Bonding to Silanols", Department of Chemistry, Imperial College of Science, Technology and Medicine, London SW7 2AY, UK.
Beam, K.E., "Anisotropic Etching of Silicon," IEEE Transactions on Electron Devices, vol. ED-25, No. 10, Oct. 1978.
Becker, E.W.; Betz, H.; Ehrfeld, W.; Glashauser, W.; Heuberger, A.; Michel, H.J.; Munchmeyer, D.; Pongratz, S.; Siemens, R.V.; "Production of Separation Nozzle Systems for Uranium Enrichment by a Combination of X-Ray Lithography and Galvano-plastics," Naturwissenschaften, 69, (1982), 520 to 523.
Blake, C.; Gould, B.J.; 1984. "Use of Enzymes In Immunoassay Techniques. A Review," Analyst, May 1984, vol. 109, 533-547.
Brody, J.P.; Yager, P.; Goldstein, R.E.; Austin, R.H.; "Biotechnology At Low Reynolds Numbers", Biophysical Journal, vol. 71, Dec. 1996, 3430-3441.
Chen, Y.F.; Yang, J.M.; Gau, J.J.; Ho, C.M.; and Tai, Y.C.; "Microfluidic System for Biological Agent Detection", The 3rd International Conference on the Interaction of Art and Fluid Mechanics, Zurich, Switzerland, 2000.
Darst, S.A.; Ahlers, M.; Meller, P.H.; Kubalek, E.W.; Blankenburg, R.; Ribi, H.O.; Ringsdorf, H.; Kornberg, R.; "Two-dimensional crystals of streptavidin on biotinylated lipid layers and their interactions with biotinylated macromolecules," Biophys J. vol. 59, Feb. 1991, 387-396.
Feynman, Richard P.; "There's Plenty of Room at the Bottom", Journal of Microelectromechanical Systems, vol. 1, No. 1, Mar. 1992.
Gau, J.J.; Lan, E. H.; Dunn, B.; Ho, C.M.; "Enzyme-Based Electrochemical Biosensor With DNA Array Chip", Proceedings of the Fourth International Symposium on Micro Total Analysis Systems (μTAS), Enschede, The Netherlands.
Gau, J.J.; Lan, E. H.; Dunn, B.; Ho, C.M.; "A MEMS based amperometric detector for *E. coli* bacteria—using self-assembled monolayers", Biosensors & Bioelectronics, 16 (2001) 745-755.

(Continued)

*Primary Examiner*—Jon D. Epperson
*Assistant Examiner*—Jeffrey S. Lundgren
(74) *Attorney, Agent, or Firm*—Gavrilovich, Dodd & Lindsey, LLP

(57) ABSTRACT

The system includes a microfabricated electrochemical biosensor for detecting the presence and/or quantity of the target analyte in the sample reagent. The biosensor includes a substrate and at least two electrically conductive electrodes. Each of the electrical conductive electrodes consists of a single layer of an electrically conductive material. The electrodes can be fabricated on the substrate by integrated circuit technology.

39 Claims, 21 Drawing Sheets

OTHER PUBLICATIONS

Ghindilis, A.L.; Atanasov, P.; Wilkins, E.; "Enzyme-Catalyzed Direct Electron Transfer: Fundamentals And Analytical Applications", Electroanalysis 1997, 9, No. 9, 661-674.

Gorton, L.; Lindgren, A.; Larsson, T.; Munteanu, F.D.; Ruzgas, T.; Gazaryan, I.; "Direct electron transfer between heme-containing enzymes and electrodes as basis for third generation biosensors", Analytica Chimica Acta 400 (1999) 91-108.

Haussling, L.; Ringsdorf, H.; Schmitt, F.J.; Knoll, W.; "Biotin-Functionalized Self-Assembled Monolayers On Gold: Surface Plasmon Optical Studies Of Specific Recognition Reactions", Langmuir vol. 7, No. 9, Sep. 1991, 1837-1840.

Ho, C.M.; Tai, Y.C.; "Review: MEMS and Its Applications For Flow Control", Journal of Fluids Engineering, vol. 118, Sep. 1996, 437-447.

Ho, C.M.; Tai, Y.C.; "Micro-Electro-Mechanical Systems (MEMS) And Fluid Flows", Annu. Rev. Fluid Mech., 1998, 30, 579-612.

Hou, S.F.; Yang, K.S.; Fang, H.Q.; Chen, H.Y.; "Amperometric glucose enzyme electrode by immobilizing glucose oxidase in multilayers on self-assembled monolayers surface", Talanta 47, (1998) 561-567.

Howe, R.T.; Muller, R.S.; "Polycrystalline Silicon Micromechanical Beams," Journal of the Electrochemical Society: Solid State Science and Technology, Jun. 1983.

Ivnitski, D.; Abdel-Hamid, I.; Atanasov, P.; Wilkins, E.; Stricker, S.; "Application of Electrochemical Biosensors for Detection of Food Pathogenic Bacteria", Electroanalysis 2000, vol. 12, No. 5, 317-325.

Ivnitski, D.; Abdel-Hamid, I.; Atanasov, P.; Wilkins, E.; "Review: Biosensors for Detection of Pathogenic Bacteria", Biosensors & Bioelectronics 14 (1999), 599-624.

Jung, L.S.; Nelson, K.E.; Campbell, C.T.; Stayton, P.S.; Yee, S.S.; Perez-Luna, V.; Lopez, G.P.; "Surface plasmon resonance measurement of binding and dissociation of wild-type and mutant streptavidin on mixed biotin-containing alkylthiolate monolayers", Sensors Actuators B 54 (1999) 137-144.

Kane, R.S.; Takayama, S.; Ostuni, E.; Ingber, D.E.; Whitesides, G.M.; "Patterning proteins and cells using soft lithography", Biomaterials 20 (1999) 2363-2376.

Lahiri, J.; Ostuni, E.; Whitesides, G.M.; "Patterning Ligands on Reactive SAMs by Microcontact Printing", Langmuir (1999) 15, 2055-2060.

Lindgren, A.; Munteanu, F.-D.; Gazaryan, I.G.; Ruzgas, T.; Gorton, L.; "Comparison of rotating disk and wall-jet electrode systems for studying the kinetics of direct and mediated electron transfer for horseradish peroxidase on a graphite electrode", J. Electroanal. Chem. 458 (1998), 113-120.

Marrazza, G.; Chianella, I.; Mascini, M., "Disposable DNA Electrochemical Biosensors for Environmental Monitoring", Analytica Chimica Acta 387 (1999), 297-307.

Motesharei, K.; Myles, D.C.; "Molecular Recognition on Functionalized Self-Assembled Monolayers of Alkanethiols on Gold", J. Am. Chem. Soc. (1998) 120, 7328-7336.

Murthy, A.S.N.; Sharma, J.; "Glucose oxidase bound to self-assembled monolayers of bis(4-pyridyl) disulfide at a gold electrode: Amperometric determination of glucose", Anal. Chim. Acta 363 (1998) 215-220.

Nathanson, H.C.; Newell, W.E.; Wickstrom, R.A.; Davis, J.R., Jr.; "The Resonant Gate Transistor", IEEE Transactions on Electron Devices, Mar. 1967.

Ooka, A.; Kuhar, K.; Cho, N.; Garrell, G.; "Surface Interactions of a Homologous Series of a,w-Amino Acids on Colloidal Silver and Gold", Biospectroscopy 5, 9-17 (1999).

Ostuni, E.; Yan, L.; Whitesides, G.M.; "The interaction of proteins and cells with self-assembled monolayers of alkanethiolates on gold and silver", Colloids Surfaces B 15 (1999) 3-30.

Rao, J.; Yan, L.; Xu, B.; Whitesides, G.M.; "Using Surface Plasmon Resonance to Study The Binding of Vancomycin and Its Dimer to Self-Assembled Monolayers Presenting D-Ala-D-Ala", J. Am. Chem. Soc. (1999) 121, 2029-2030.

Revell, D.J.; Knight, J.R.; Blyth, D.J.; Haines, A.H.; Russell, D.A.; "Self-Assembled Carbohydrate Monolayers: Formation And Surface Selective Molecular Recognition", Langmuir (1998) 14 4517-4524.

Ruzgas, T.; Gorton, L.; Emne'us, J.; Marko-Varga, G.; "Kinetic models of horseradish peroxidase action on a graphite electrode", J. Electroanal. Chem. 391 (1995) 41-49.

Ruzgas, T.; Csöregi, E.; Emnéus, J.; Gorton, L.; Marko-Varga, G.; "Peroxidase-modified electrodes: Fundamentals and application", Analytica Chimica Acta 330 (1996), 123-138.

Sieval, A.; Demirel, A.; Nissink, J.; Linford, M.; Van Der Maas, J.; De Jeu, W.; Zuilhof, H.; Sudhölter, E.; "Highly Stable Si-C Linked Functionalized Monolayers on the Silicon(100) Surface", Langmuir 1998, 14, 1759-1768.

Sigal, G.; Bamdad, C.; Barberis, A.; Strominger, J.; Whitesides, G.M.; "A Self-Assembled Monolayer for the Binding and Study of Histidine-Tagged Proteins by Surface Plasmon Resonance", Anal. Chem., 1996, 68, 490-497.

Spinke, J.; Liley, M.; Guder, H.J.; Angermaier, L.; Knoll, W.; "Molecular Recognition at Self-Assembled Monolayers: The Construction of Multicomponent Multilayers", Langmuir (1993) 9 (7), 1821-1825.

Sun, X.; He, P.; Liu, S.; Ye, Jiannog; Fang, Y.; "Immobilization of single-stranded deoxyribonucleic acid on gold electrode with self-assembled aminoethanethiol monolayer for DNA electrochemical sensor applications", Talanta 47 (1998) 487-495.

Taylor, Robert; "Bioterrorism Special Report: All fall down", New Scientist, vol. 150, Issue 2029, May 11, 1996.

Trimmer, W.S.N.; "Microrobots and Micromechanical Systems", Sensors and Actuators, 19, Sep. 1989, 267-287.

Trimmer, William; "Grand in Purpose, Insignificant in Size" The Tenth Annual International Workshop on MEMS, Nagoya, Japan, Proceedings IEEE Catalog No. 97CH36021, 1997, 9-13.

Wagner, P.; Hegner, M.; Guntherodt, H-J; Semenza, G., "Formation and in Situ Modification of Monolayers Chemisorbed on Ultraflat Template-Stripped Gold Surfaces," Langmuir 11 (1995) 3867-75.

Wang, J.; Rivas, G.; Cai, X.; Palecek, E.; Nielsen, P.; Shiraishi, H.; Dontha, N.; Luo, D.; Parrado, C.; Chicharro, M.; Farias, P.; Valera, F.; Grant, D.; Ozsoz, M.; Flair, M.; "DNA electrochemical biosensors for environmental monitoring. A Review", Anal. Chim. Acta 347, (1997) 1-8.

Wang, T.; Chen Y.; Masset S.; Ho, C.; Tai, Y.; "Molecular Beacon Based Micro Biological Detection System", Proceedings of the 2000 International Conference on Mathematics and Engineering Techniques in Medicine and Biological Sciences (METMBS'2000) Las Vegas, NV.

Weber, P.; Ohlendorf, D.; Wendoloski, J.; Salemme, F.; "Structural Origins of High-Affinity Biotin Binding to Streptavidin", Science (1989) 243, 85-88.

Whitesides, G.; Laibinis, P., "Wet Chemical Approaches to the Characterization of Organic Surfaces; Self-Assembled Monolayers, Wetting, and the Physical-Organic Chemistry of the Solid-Liquid Interface," Langmuir 1990, 6, 87.

Wink, T; Van Zuilen, S.; Bult, A.; Van Bennekom, W., "Self-assembled Monolayers for Biosensors", Analyst, Apr. 1997, 122, 43R-50R.

Xia, Y.; Whitesides, G.; "Soft Lithography", Angew. Chem. Int. Ed. (1998) 37, 550-575.

Yang, R.; Wang, K.; Xiao, D.; Luo, K.; Yang, X.; "A renewable liquid drop sensor for di- or trinitrophenol based on fluorescence quenching of 3,3 A, 5,5 A—tetramethylbenzidine dihydrochloride", Analyst, 2000, 125, 877-882.

"USAF Pamphlet on the Medical Defense Against Biological Material—Medical Defense Against Biological Material", Defense Technical Information Center, Feb. 11, 1997.

Cussler, E. L.; Diffusion—mass transfer in fluid systems, $2^{nd}$ edition, Cambridge University Press, 1997.

Dunford, H.B.; Horseradish peroxidase: structure and kinetic properties. In: Everse, J., Everse, K.E., Grisham, M.B. (Eds.), Peroxidases in Chemistry and Biology, vol. 2. CRC Press, Boca Raton, FL, 1991, pp. 1-24.

Eggins, B.; "Biosensors," John Wiley and Sons, 1996, New York.

Ehteshami, G.; Rana, N.; Raghu, P.; Shadman, F.; "Interactions of impurities with Silicon and Silicon dioxide during oxidation", Center for Micro-contamination Control, NSF I/U CRC.

Hall, E.A.H.; "Biosensors", Prentice Hall, Englewood Cliffs, New Jersey, 1991.

Kevles, D.; L. Hood; "The Code of Codes: Scientific and Social Issues in the Human Genome Project", Harvard University Press, Cambridge, Mass., 1992.

Ulman, A.; "Ultrathin Organic Films from Langmuir Blodgett to Self-Assembly", Academic Press: New York, 1991.

Ulman, A.; "An Introduction to Ultrathin Organic Films From Langmuir Blodgett to Self-Assembly", Academic Press, Inc., San Diego, CA, 1991.

Ulman, A., Ed.; "Characterization of Organic Thin Films", Butterworth-Heinemann: Boston, 1995.

Voet, Donald; Voet, J.; "Biochemistry, $2^{nd}$ edition" Wiley, New York, 916-919.

Wise, K.; Jackson, T.; Masnari, N.; Robinson, M.; Solomon, D.; Wuttke, G.; Rensel, W.; "Fabrication of Hemispherical Structures Using Semiconductor Technology for Use in Thermonuclear Fusion Research", Journal of Vacuum Science Technology, May/Jun. 1979.

Berger et al., *Surface Stress in the Self-Assembly of Alkanethiols in Gold Probed by a Force Microscopy Technique*, Appl. Phys. A 66, S55-S59 (1998).

Dubois et al., *Synthesis, Structure, and Properties of Model Organic Surfaces*, Annu. Rev. Phys. Chem. 1992, 43:437-63.

Knobler et al., *Phase Transitions in Monolayers*, Annu. Rev. Phys. Chem. 1992, 25:207-36.

Kokkoli et al., *Effects of Solvents on Interactions Between Hydrophobic Self-Assembled Monolayers*, Journal of Colloid and Interface Sciences 209, 60-65 (1999).

Lyons, Michael E.G., *Mediated Electron Transfer at Redox Active Monolayers*, Sensors 2001, 1, 215-228.

Lyons, Michael E.G., *Mediated Electron Transfer at Redox Active Monolayers. Part 2:Analysis of the Chromoamperometric response to Potential Step Perturbation*, Sensors 2002, 2, 314-330.

Lyons, Michael E.G., *Mediated Electron Transfer at Redox Active Monolayers. Part 3: Biomolecular Outer-Sphere, First Order Koutecky-Levich and Adduct Formation Mechansims*, Sensors 2002, 2, 473-506.

Lyons, Michael E.G., *Mediated Electron Transfer at Redox Active Monolayers. Part 4: Kinetics of Redox Enzymes Coupled with Electron Mediators*, Sensors 2003, 3, 19-42.

Mrksich et al., *Using Self-Assembled Monolayers to Understand the Interactions of Man-Made Surfaces with Proteins and Cells*, Annu. Rev. Biophys. Biomol. Struct. 1996, 25:55-78.

Rau et al., Measurement of the Repulsive Force Between Polyelectrolyte Molecules in Ionic Solution: Hydration Forces Between Parallel DNA Double Helices, Proc. Natl. Acad. Sci. USA, vol. 81, pp. 2621-2625, May 1984, Biochemistry.

Schreiber, Frank, *Self-Assembled Monolayers: From 'Simple' Model Systems to Biofunctionalized Interfaces*, J. Phys.: Condens. Matter 16 (2004) R881-R900.

Schwartz, Daniel K., *Mechansims and Kinetics of Self-Assembled Monolayer Formation*, Annu. Rev. Phys. Chem. 2001, 52:107-37.

Valignant et al., *Reversible Self-Assembly and Directed Assembly of DNA-Lined Micrometer-Sized Colloids*, PNAS, Mar. 22, 2005, vol. 102, No. 12, 4225-4229.

* cited by examiner

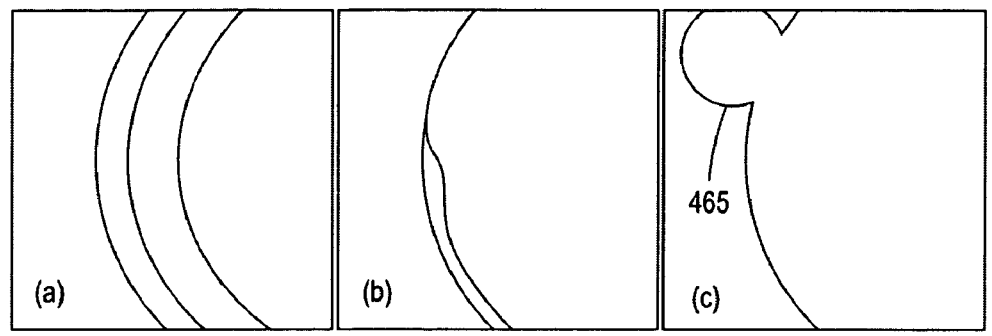
Figure 11
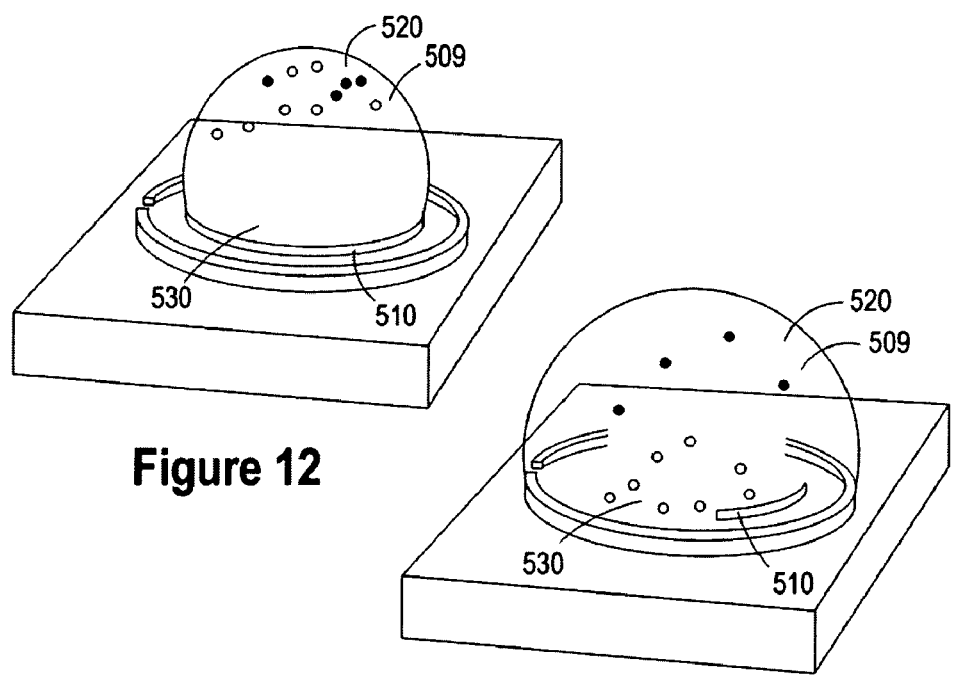
Figure 12
Figure 13

$P_R$: Reduced Peroxidase   $P_O$: Oxidized Peroxidase
$M_O$: Oxidized Mediator    $M_R$: Reduced Peroxidase Comparison of various reagents for the desorption of streptavidin from
surface as determined by surface plasmon resonance

| Treatment Condition | Streptavidin on Bare Au ~2400 RU deposited Loss in Signal (RU) | | Streptavidin on biotin-DAD-C12-SH/Au ~3000 RU deposited Loss in Signal (RU) | | Streptavidin on biotin-HPDP/Au ~1700 RU deposited Loss in Signal (RU) | |
|---|---|---|---|---|---|---|
| 1.0 M KCl | 0 | 0 | 0 | 0 | 0 | 0 |
| 8 M Urea | 280(12%) | 370(15%) | 790(26%) | 1050(35%) | 360(21%) | 300(18%) |
| 0.5% SDS | 40(2%) | 150(6%) | 390(13%) | 230(8%) | 330(19%) | 690(40%) |
| 0.1 M HCl | 0 | 0 | 0 | 0 | 0 | 0 |
| 0.1 NaOH | 400(17%) | 550(23%) | 630(21%) | 690(23%) | 400(24%) | 200(12%) |
| 40% Formamide | 0 | 0 | 0 | 0 | 0 | 0 |

Figure 42

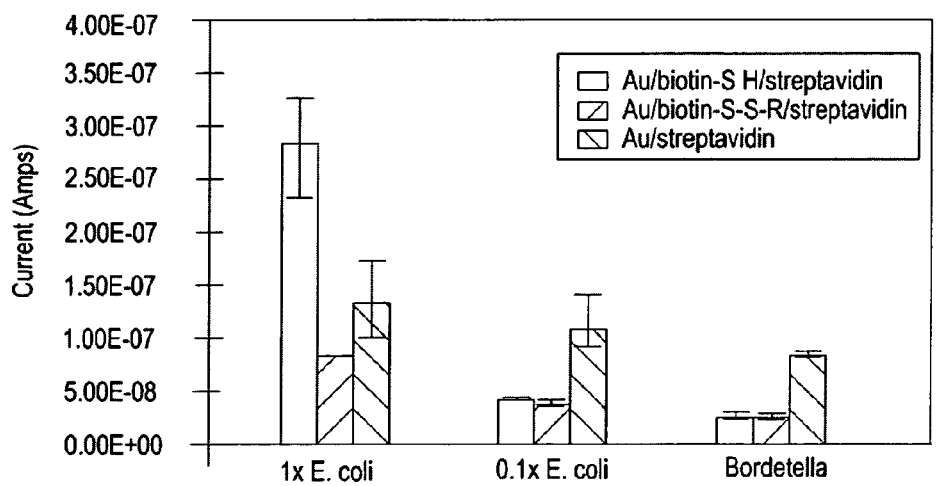

Figure 43

SEQUENCE LISTING

```
<160> NUMBER OF SEQ ID NOS: 26

<210> SEQ ID NO 1
<211> LENGTH: 1447
<212> TYPE: DNA
<213> ORGANISM: Escherichia coli
<220> FEATURE:
<221> NAME/KEY: modified_base
<222> LOCATION: (314)
<223> OTHER INFORMATION: a, t, c, g, other or unknown
<221> NAME/KEY: modified_base
<222> LOCATION: (555)..(556)
<223> OTHER INFORMATION: a, t, c, g, other or unknown
<221> NAME/KEY: modified_base
<222> LOCATION: (628)
<223> OTHER INFORMATION: a, t, c, g, other or unknown
<221> NAME/KEY: modified_base
<222> LOCATION: (1424)..(1426)
<223> OTHER INFORMATION: a, t, c, g, other or unknown

<400> SEQUENCE: 1
tgatcatggc tcagattgaa cgctggcggc aggcctaaca catgcaagtc gaacggtaac      60
aggaagaagc ttgctctttc gctgacgagt ggcggacggg tgagtaatgt ctgggaaact     120
gcctgatgga gggggataac tactggaaac ggtagctaat accgcataac gtcgcaagac     180
caaagagggg gaccttcggg cctcttgcca tcggatgtgc ccagatggga ttagctagta     240
ggtggggtaa cggctcacct aggcgacgat ccctagctgg tctgagagga tgaccagcca     300
cactggaact gagncacggt ccagactcct acgggaggca gcagtgggga atattgcaca     360
atgggcgcaa gcctgatgca gccatgccgc gtgtatgaag aaggccttcg ggttgtaaag     420
tactttcagc ggggaggaag ggagtaaagt taatacctt gctcattgac gttacccgca      480
gaagaagcac cggctaactc cgtgccagca gccgcggtaa tacggagggt gcaagcgtta     540
atcggaatta ctggnngtaa agcgcacgca ggcggttttgt taagtcagat gtgaaatccc     600
cgggctcaac ctgggaactg catctganac tggcaagctt gagtctcgta gagggggta      660 gaattccagg tgtagcggtg aaatgcgtag agatctggag gaataccggt ggcgaaggcg     720 gcccctgga cgaagactga cgctcaggtg cgaaagcgtg gggagcaaac aggattagat     780
accctggtag tccacgccgt aaacgatgtc gacttggagg ttgtgcccct gaggcgtggc     840
```

```
ttccggagct aacgcgttaa gtcgaccgcc tgggagtac ggccgcaagg ttaaaactca      900
aatgaattga cggggccgc acaagcggtg gagcatgtgg tttaattcga tgcaacgcga      960
agaaccttac ctggtcttga catccacgga agttttcaga gatgagaatg tgcttcggga   1020
accgtgagac aggtgctgca tggctatcat cagctcgtgt tgtgaaatgt tgggttaagt   1080
cccgcaacga gcgcaaccct tatcctttgt tgccagcggt ccggccggga actcaaagga   1140
gactgccagt gataaactgg aggaaggtgg ggatgacgtc aagtcatcat ggcccttacg   1200
accagggcta cacacgtgct acaatggcgc atacaaagag aagcgacctc gcgagagcaa   1260
gcggacctca taaagtgcgt cgtagtccgg attggagtct gcaactcgac tccatgaagt   1320
cggaatcgct agtaatcgtg gatcagaatg ccacggtgaa tacgttcccg ggccttgtac   1380
acaccgcccg tcacaccatg ggagtgggtt gcaaagaag tagnnngctt aaccttcggg   1440
agggcgc                                                              1447

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 2
ggtaacggct cacctaggc                                                   19

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 3
ccagatggga ttagctagta gg                                               22

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 4
gaccagggct acacacgtg                                                   19

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 5
gtaacggctc acctaggcg                                                   19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Primer
```

```
<400> SEQUENCE: 6
gggtaacggc tcacctagg                                                19

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 7
taacggctca cctaggcga                                                19

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 8
cccagatggg attagctagt                                               20

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 9
aaacgatgtc gacttggag                                                19

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 10
aggcgacgat ccctagctg                                                19

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 11
taaacgatgt cgacttggag                                               20

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 12
gaagtcggaa tcgctagtaa t                                             21

<210> SEQ ID NO 13
<211> LENGTH: 19
```

```
<212> TYPE: DNA
<213> ORGANISM: Artificial Sequence
<220> FEATURE:
<223> OTHER INFORMATION: Description of Artificial Sequence: Primer

<400> SEQUENCE: 13
aagaccaaag aggggggacc                                                    19

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 14 ccgttaccccc acctactagc                                                   20

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 15
tagggatcgt cgcctaggt                                                     19

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 16
gccgttaccc cacctactag                                                    20

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 17
ctagggatcg tcgcctagg                                                     19

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 18
cgccattgta gcacgtgtg                                                     19

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 19
```

-continued agggatcgtc gcctaggtg                                                19

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 20 cgttaccccca cctactagct                                              20

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 21 cgttaccccca cctactagct a                                            21

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 22
ctgatccacg attactagcg                                               20

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 23
tcctctcaga ccagctagg                                                19

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 24
aagggcacaa cctccaagt                                                19

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 25
tcatcctctc agaccagcta g                                             21

<210> SEQ ID NO 26
<211> LENGTH: 22
<212> TYPE: DNA
<213> ORGANISM: Artificial Sequence -continued

```
<220> FEATURE:
<223> OTHER INFORMATION: Description of Artificial Sequence:
      Illustrative nucleotide

<400> SEQUENCE: 26
gtaacctgtg tgaacacaga tc                                                  22
```

BIOLOGICAL IDENTIFICATION SYSTEM WITH INTEGRATED SENSOR CHIP

This application claims the benefit of U.S. Provisional Patent Application Ser. No. 60/201,603, filed May 3, 2000.

STATEMENT REGARDING FEDERALLY SPONSORED RESEARCH OR DEVELOPMENT

This invention was made with Government support under Grant No. N66001-96-C-8632 awarded by the Department of the Navy. The Government has certain rights in this invention.

FIELD OF THE INVENTION

The field of the present invention relates generally to apparatus and methods for sensing or detecting various target analytes, including ionic molecules (e.g. iron, chromium, lead, copper, calcium or potassium) and macromolecules (e.g. DNA, RNA or protein) and in particular, to biosensors, methods of using the biosensors, and methods for making the biosensors.

BACKGROUND OF THE INVENTION

A variety of biosensors have been developed for the detection of biological material, such as pathogenic bacteria. Conventional methods for detecting bacteria usually involve a morphological evaluation of the organisms and rely on (or often require) growing the number of organisms needed for such an evaluation. Such methods are time consuming and are typically impractical under field conditions. The need for rapid detection as well as portability has led to the development of systems that couple pathogen recognition with signal transduction.

Requirements for an ideal detector include high specificity and high sensitivity using a protocol that can be completed in a relatively short time. Moreover, systems that can be miniaturized and automated offer a significant advantage over current technology, especially if detection is needed in the field.

The electrochemical methods use the principle of electrical circuit completion. To complete the electrical circuit, a counter electrode is used to provide a return path to the sample solution or reagent and a reference electrode is used as a reference point against which the potential of another electrode or electrodes are determined (typically that of the working electrode or measuring electrode). Since this contact must be provided by electrochemical means, i.e. a metal electrode immersed in a chemical solution or reagent, it is impossible to avoid generating an electrical potential in series with the potential developed by the electrode. The conventional theory in the electrochemical methods is that it is essential for the reference electrode potential to be very stable and not be affected by chemical changes in the solution. Thus, silver/silver chloride reference electrodes, which provide a very stable reference potential, are the most common type of electrode used for reference electrodes today.

Referring to FIG. 1, the typical silver/silver chloride reference electrode 10 contains a chloridised silver wire 1 (a layer of silver chloride coated on silver wire) immersed in a solution 5 of potassium chloride (3.5M KCl) saturated with silver chloride (AgCl). This internal filling solution 5 slowly seeps out of the electrode 10 through a porous ceramic junction 20 and acts as an electrical connection between the reference element 1 and the sample. Potassium chloride is used because it is inexpensive and does not normally interfere with the measurement. The solution 5 also includes silver chloride to prevent dissolution of the coating on the reference element 1. It is therefore necessary to maintain the level of solution 5 in the electrode 10 using a filling solution hole 40. This technique, however, is not robust and precise. In addition, it requires two-layered reference electrode (e.g., silver chloride coated on silver) having a known reference electrode potential described above.

Referring now to FIG. 2, the electrochemical methods also required a potentiostat 50, which is a control amplifier with the test cell placed in the feedback loop. The objective is to control the potential difference between a test electrode (working electrode) 60 and a reference electrode 70 by the application of a current via the third, auxiliary electrode (counter electrode) 80. In practice a fairly good potentiostat may be built using a minimum of components. In the circuit shown here, 90A and 90B are 1.22V bandgap reference diodes connected between the positive and negative power rails. Potentiometer 100 is then used to set the required cell polarization, applied to the non-inverting input of the main amplifier 110. The working electrode 60 connects to the ground of the circuit and the reference electrode 70 to the inverting input of the main amplifier 110. In order to boost the output capability somewhat (most operational amplifiers are limited to about 20 mA and do not tolerate capacitative loads well) a unity gain buffer amplifier 120 is used. Preferably, gain buffer amplifier 120 has a much higher bandwidth than amplifier 110, otherwise the circuit is likely to oscillate when driving a capacitative cell. The output of the buffer amplifier 120 connects to the auxiliary electrode 80 via a current measuring resistor 140. Differential amplifier 130 is then used to measure the voltage drop across this resistor 140 and to convert it to a ground referenced output voltage.

Microelectromechanical systems (MEMS) technology provides transducers to perform sensing and actuation in various engineering applications. The significance of MEMS technology is that it makes possible mechanical parts of micron size that can be integrated with electronics and batch fabricated in large quantities. MEMS devices are fabricated through the process of micromachining, a batch production process employing lithography. Micromachining relies heavily on the use of lithographic methods to create 3-dimensional structures using pre-designed resist patterns or masks. MEMS is one suitable technology for making microfabricated devices or aspects thereof. Microfabricated devices are generally defined as devices fabricated by using MEMS and/or integrated circuit (IC) technology. An IC is defined as a tiny chip of substrate material upon which is etched or imprinted a complex of electronic components and their interconnections. However, MEMS technology has not been successfully integrated with biosensing methods to detect various ionic molecules and macromolecules (DNA, RNA or protein), especially with electrochemocal methods, to provide biosensors with miniaturization and portability.

Existing techniques in biosensing of bacteria do not achieve high specificity and sensitivity with high dimensional precision. The detection is typically not applicable to a broad range of pathogenic bacteria. In addition, conventional biosensors are not miniaturized into a portable instrument.

Accordingly, there is a need to have a technique that can overcome the above disadvantages.

BRIEF DESCRIPTION OF THE DRAWINGS

In the drawings, wherein the same reference number indicates the same element throughout the several views:

FIGS. 11(a), (b) and (c) are diagrams showing reagent and/or solution confinement by surface tension and treatment according to the present invention.

FIG. 12 is a diagram showing reagent and/or solution confinement selectively over only a working electrode on a biosensor according to the present invention.

FIG. 13 is a diagram showing reagent and/or solution confinement over all electrodes on a biosensor according to the present invention.

FIG. 42 is a graph on the result of an experiment that compares the efficacy of the immobilized streptavidin to capture the biotin-rRNA-POD hybrid.

FIG. 43 is a graph showing the result of using *E. coli* and *Bordetella* to determine the sensitivity of the system.

DESCRIPTION

Figure 1:
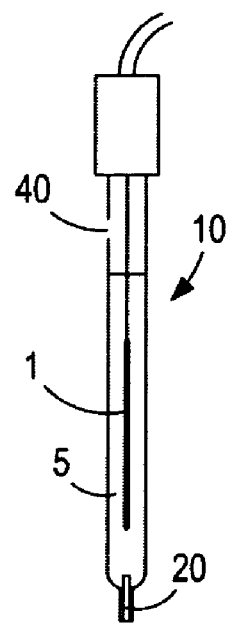
FIG. 1 is a schematic of an embodiment of a conventional reference electrode.
Figure 2:
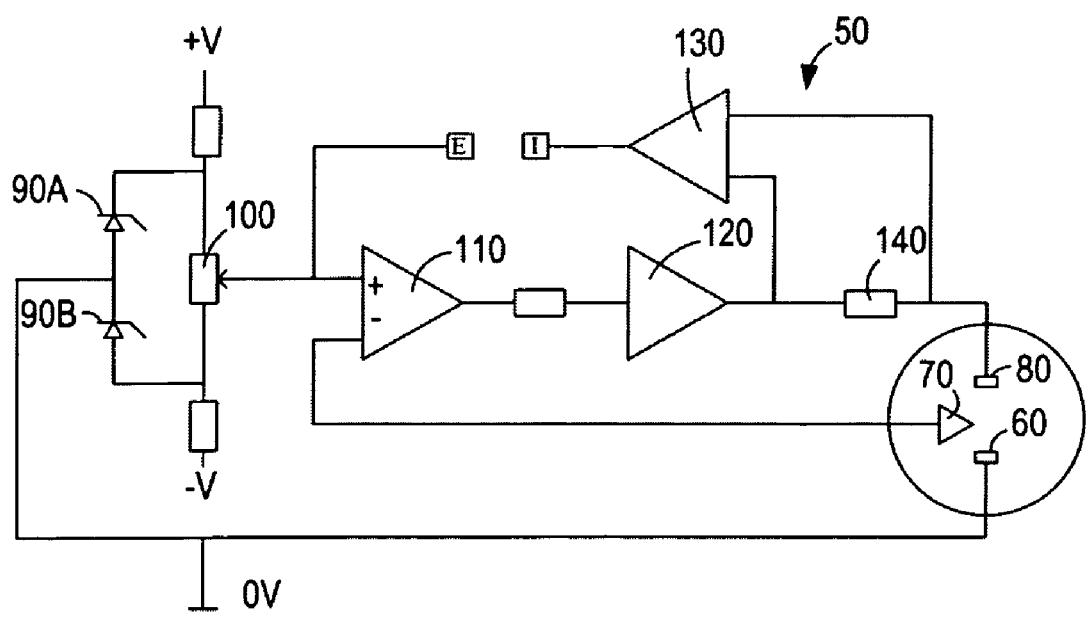
FIG. 2 is a schematic of an embodiment of a potentiostat used in the electrochemical methods.

Although specific embodiments of the invention will now be described with reference to the drawings, it should be understood that various changes and modifications may be made without departing from the spirit, scope and contemplation of the invention. Indeed, the drawings and description herein are provided by way of examples, and not by way of limitations.

A first aspect of the present invention provides an apparatus and method for sensing or detecting various target analytes, including especially macromolecules (e.g. DNA, RNA or protein) and ionic molecules (e.g. iron, chromium, lead, copper, calcium or potassium) using a biosensor incorporated on a single substrate (silicon, glass, plastic, etc.). The substrated biosensor system comprises at least two electrodes that are typically fabricated together as a single series microfabrication process step on the substrate. However, successive microfabrication steps may also be employed to fabricate the system.

In a preferred embodiment, the electrodes are all made out of pure metal (as opposed to the Ag/AgC1 electrodes of the prior art, for example). In another preferred embodiment, the substrated biosensor system comprises a working electrode, a reference electrode and a counter (auxiliary) electrode. Preferably the substrated biosensor system has the same electrochemical performance as a conventional electrochemical biosensor. In addition, the substrated biosensor system should be compatible with integrated circuit (IC) and/or MEMS fabrication processes and be capable of being constructed in a small area.

A second aspect of the present invention provides an apparatus and method for confinement of reagent and/or solution in a biosensor using surface tension at small scale. The reagent and/or solution contain the necessary electrolytes and/or analytes needed for biological sensing.

In a preferred embodiment, the apparatus and method in the present invention allow for each electrode used for sensing or detecting various ionic molecules (e.g. iron, chromium, lead, copper, calcium or potassium) and macromolecules (e.g. DNA, RNA or protein) to be in selective contact with the reagent and/or solution when the electrolytes and/or analytes are needed by using controllable surface properties and surface tension forces at small scale.

In another preferred embodiment, the apparatus and method for confinement of reagent and/or solution (and thus the electrolytes and/or analytes in the reagent and/or solution) using surface tension is incorporated with a portable or hand-held device and is immune to shaking of the device. In addition, the reagent and/or solution should be held firmly in position by the biosensor using surface tension even when the biosensor is flipped upside down.

A third aspect of the present invention provides an apparatus and method for integrating the components of an electrochemical sensor and/or sensors (e.g. electrodes) and additional required electronic circuit components (e.g. amplifiers) in an electrochemical sensor or sensors with integrated circuit (IC) technologies. The entire sensor system and/or systems can be incorporated on a single IC substrate or chip, such as a single semiconductor (e.g. silicon or gallium arsenide) substrate or chip. Preferably, no or much fewer external components and/or instruments are required to complete the system or systems. The sensor and/or sensors are preferably fabricated using the IC process.

In any of the embodiments used for macromolecule electrochemical detection, a preferred feature of the invention is to modify the surface on at least one of the electrodes. Preferably, the surface is modified for anchoring macromolecules on the surface. Preferably, the surface is modified using a self-assembly monolayer (SAM) such as biotin-streptavidin. Preferably, the SAM is placed on the surface of a working electrode in an electrochemical sensor. Optionally, materials such as sol gel and/or carbon paste may be used to modify the surface (as a replacement for SAM or in combination with SAM).

One embodiment of the present invention provides a robust and precise biological detection using electrochemical methods. Redox (reduction-oxidation) methods are used, without the need of a two-layered reference electrode (e.g., silver chloride coated on silver) having a known reference electrode potential as in the prior art techniques.

One embodiment of the present invention uses an effective means of achieving high specificity by detecting the bacteria's genetic material (e.g. rRNA, mRNA, denatured DNA). By choosing a single-stranded DNA (ssDNA) probe whose sequence is complementary only to the target bacteria's rRNA or ssDNA, monitoring the hybridization event allows selective sensing of target cells. To maximize sensitivity, coupling the hybridization event with an enzymatic reaction leads to signal amplification, as each substrate-to-product turnover contributes to the overall signal. Biosensing to detect DNA hybridizations that are amplified by enzymatic reaction can still be completed within a reasonably short time according to the invention.

A prototype amperometric detector for *Escherichia coli* (*E. coli*) based on the above determinations and technologies is described in the following. The technologies of MEMS, self-assembled monolayers (SAMs), DNA hybridization, and enzyme amplification all contribute to the design of a miniaturized, specific, and sensitive *E. coli* detector. DNA electrochemical probes typically use graphite or carbon electrodes. Commercial units for amperometric detection of DNA from *E. coli* using screen-printed carbon electrodes on disposable test strips are also available. Screen-printing has the advantage of low cost; however, achieving high dimensional precision is not easy. One embodiment of the present invention develops a method of using lithography to accurately pattern in μm size dimensions a wide range of materials such as metals (e.g. Au, Ag) and carbon. Moreover, utilizing a surface modification, such as self-assembly monolayer (SAM) of biotin-DAD-C12-SH dodecanamide, is a preferred method of selectively immobilizing molecules on MEMS surfaces. The formation of SAMs on Au, Ag and other metals has been well studied, and proteins and other biomolecules can be easily immobilized onto surfaces such as Au using SAMs. Amperometric methods using SAMs on electrodes have demonstrated the ability to detect target analytes successfully.

In the instant *E. coli* detection system, one embodiment of the present invention identifies and takes advantage of certain benefits inherent in each technology. Using DNA hybridization and enzyme amplification, the present invention achieves the required specificity and sensitivity. Using MEMS and SAMs, one embodiment of the present invention fabricates a miniaturized system that can be developed into a portable instrument. Finally, the invention demonstrates that the present detection system is applicable to a broad range of pathogenic bacteria. For example, the detection module and assay protocol can be adapted to detect uropathogenic *E. coli* and identify microorganisms causing otitis media (middle ear infection).

The first aspect of the invention relates to detection of various target analytes, especially ionic molecules (e.g. iron, chromium, lead, copper, calcium or potassium) and macromolecules (e.g. DNA, RNA or protein), using the principles of electrochemical detection. The principles of electrochemical detection require the use of a redox cell and an electrochemical reaction in the cell.

The redox cell is a device that converts chemical energy into electrical energy or vice versa when a chemical reaction occurs in the cell. Typically, the cell consists of three electrodes immersed into an aqueous solution (electrolyte) with electrode reactions occurring at the electrode-solution surfaces.

The cell consists of two electronically conducting phases (e.g., solid or liquid metals, semiconductors, etc.) connected by an ionically conducting phase (e.g. aqueous or nonaqueous solution, molten salt, ionically conducting solid). As an electrical current passes, it changes mode from electronic current to ionic current and back to electronic current. These changes of conduction mode are accompanied by reduction-oxidation reactions. Each mode changing reaction is called a half-cell.

Each electrochemical reaction is reduction-oxidation (redox) reaction that occurs in the redox cell. For example, in a spontaneous "chemical reaction" during the oxidation of hydrogen by oxygen to water, electrons are passed directly from the hydrogen to the oxygen. In contrast, in the spontaneous electrochemical reaction in the redox cell, two separate electrode reactions occur substantially simultaneously or in tandem.

An important feature of the redox cell is that the simultaneously occurring reduction-oxidation reactions are spatially separated. The hydrogen, for example, is oxidized at the anode electrode by transferring electrons to the anode electrode and the oxygen is reduced at the cathode electrode by accepting electrons from the cathode electrode. The overall electrochemical reaction is the sum of the two electrode reactions. The ions produced in the electrode reactions, in this case positive hydrogen ions and negative hydroxyl ions, will recombine in the solution to form the final product of the reaction: water.

During this process the electrons are conducted from the anode electrode to the cathode electrode through an outside electric circuit where the electronic current can be measured. The reaction can also be reversed; water can be decomposed into hydrogen and oxygen by the application of electrical power in an electrolytic cell.

A three-electrode system of the invention is an electrochemical cell containing a working electrode, a counter electrode (or auxiliary electrode), and a reference electrode. A current may flow between the working and counter electrodes, while the potential of the working electrode is measured against the reference electrode. This setup can be used in basic research to investigate the kinetics and mechanism of the electrode reaction occurring on the working electrode surface, or in electroanalytical applications. The detection module in the preferred embodiment in the instant invention is based of a three-electrode system.

The counter electrode is used to make an electrical connection to the electrolyte so that a current can be applied to the working electrode. The counter electrode is usually made of inert materials (noble metals or carbon/graphite) to avoid its dissolution. It has been observed in connection with the present invention that a small feature or small cross-section at the counter electrode will heat up the surrounding solution when a large current is pulled out from the counter electrode. Bubbles will be generated if the current is continuously overflowed, and ultimately dissolution of the electrode occurs. Thus, the bubble formation can be avoided by controlling the current and/or the electrode size. In a preferred embodiment of the present invention, the width of the counter electrode is large enough to avoid this heat up problem even at large current.

The reference electrode is used as a reference point against which the potential of other electrodes (typically that of the working electrode or measuring electrode) can be measured in an electrochemical cell. The few commonly used (and usually commercially available) electrode assemblies all have an electrode potential independent of the electrolyte used in the cell, such as a silver/silver-chloride electrode, calomel electrode, or hydrogen electrode. However, a single layer electrode, such as a single layer of gold electrode, can fulfill the requirement for a reference electrode. In addition, other materials such as silver, copper, platinum, chromium, aluminum, titanium, nickel may also work as a single layer reference electrode under the right conditions.

The working electrode plays a central role in the electrochemical biosensors of the invention. The reaction occurring at the working electrode may be used to perform an electrochemical analysis of the electrolyte solution. It can serve either as an anode or a cathode, depending on the applied polarity. One of the electrodes in some "classical two-electrode" cells can also be considered a "working" ("measuring," "indicator," or "sensing") electrode, e.g., in a potentiometric electroanalytical setup where the potential of the measuring electrode (against a reference electrode) is a measure of the concentration of a species in the solution.

In a preferred three-electrode embodiment, the counter and reference electrodes are configured to extend generally about the periphering of the working electrode of the biosensor. Suitability configurations are seen in, for example, FIGS. 3, 4, 5, 12, 13 and 23.

Figure 3:
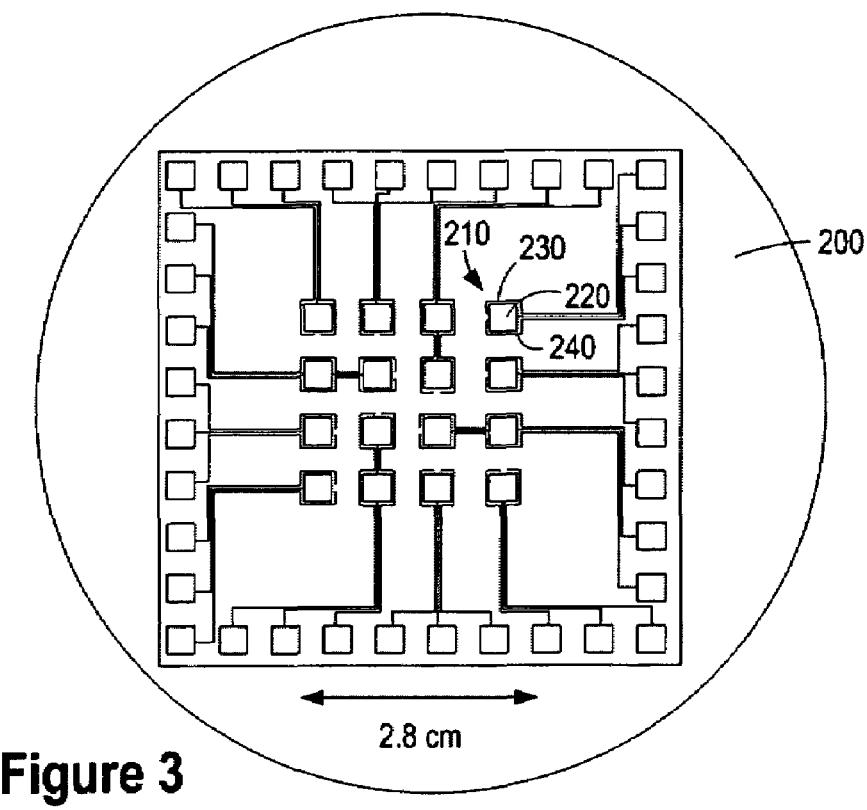
FIG. 3 is a schematic of an embodiment of a plurality of electrochemical biosensors on a circular substrate wafer according to the present invention.

In a preferred embodiment, the electrochemical biosensor is fabricated using microelectromechanical systems (MEMS) technology. Referring now to FIG. 3, a layer of silicon dioxide ($SiO_2$, 1000 Å) is deposited on a bare silicon wafer 200 (prime grade, p-type <100>, thickness 500-550. μm) and served as a pad layer underneath the silicon nitride ($Si_3N_4$, 1000 Å) to release stress and improve adhesion. A plurality of MEMS biosensors (such as biosensor 210) were fabricated with working electrodes of various dimensions (such as working electrode 220). Preferably each of the working electrodes is etched to form a well up to 350 μm in depth.

The nitride-coated silicon wafer 200 was patterned and bulk etched using KOH along the [111] and [100] crystal planes, and the depth of the well was controlled by KOH etching time and temperature. The 100. μm wide auxiliary (such as auxiliary electrode 230) and reference (such as reference electrode 240) electrodes are separated from their corresponding working electrode 220 by 200 μm. FIG. 3 shows a schematic of the pattern used in generating the MEMS biosensors (such as biosensor 210).

The nitride and oxide were removed by HF etching to release internal stress, and another oxide layer (5000 Å) was deposited for electrical isolation. Electrodes were patterned by PR5214 photo resist reverse imaging and lift-off process with electron beam deposition of Au(2000 Å)/Cr(200 Å). Finally the wafer 200 was bathed in hexamethyldisilazane (HMDS) vapor for three minutes after ten minutes of a 150° C. hot bake to generate a hydrophobic surface on the surrounding Si areas. The hydrophobic nature of the surrounding area, along with the 3-dimensional nature of the working electrode (such as working electrode 220), allows containment of a liquid droplet on the working electrode 220 during the initial sensing step of immobilizing to the working electrode molecules of interest in the solution. This design effectively minimized non-specific binding of biomolecules to other areas of the MEMS array.

Preferably the material used for all the electrochemical electrodes is gold (Au). Several conducting materials, available in MEMS technology, were patterned on a silicon substrate by the lift-off process, and the characteristics of the three-electrode system were tested by cyclic voltammetry with ferricyanide solution. Different combinations of gold, platinum, titanium and aluminum electrodes were tested and the Au/Au/Au three-electrode system gave the best C-V curve and redox characteristics.

Figure 4:
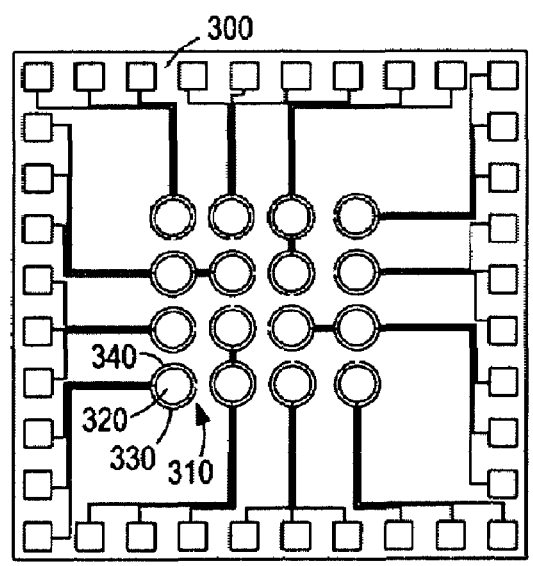
FIG. 4 is a schematic of alternative embodiment of a plurality of electrochemical biosensors on a square substrate according to the present invention.

FIG. 4 shows an embodiment of biosensors fabricated on a square substrate 300 (such as silicon, gallium arsenide, plastic and/or glass) having a plurality of circular biosensors, such as biosensor 310. The biosensor 310 comprises a working electrode 320, a reference electrode 330, and a counter (auxiliary) electrode 340. As previously mentioned, preferably the electrodes are constructed out of a single layer of conducting materials, available in MEMS technology. Furthermore, all of the electrodes should preferably be constructed out of gold (Au).

Figure 5:
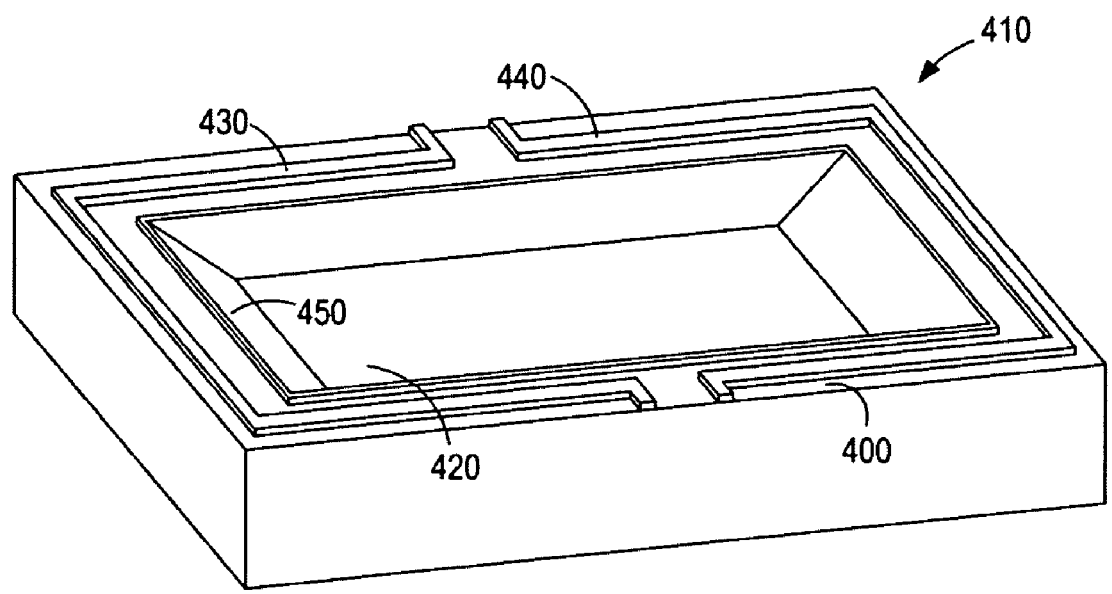
FIG. 5 is a schematic of another embodiment of an electrochemical biosensor on a substrate according to the present invention.

FIG. 5 shows yet another preferred embodiment of the present invention. The biosensor 410 comprises a working electrode 420, a reference electrode 430 and a counter (auxiliary) electrode 440 fabricated on the substrate. Preferably, the electrodes are made out of gold. The working electrode 420 is formed in a built-in well 450 in the substrate up to 350 μm in depth. The well 450 is designed for confining a desired reagent within the well-defined space. As shown in FIG. 5, the well 450 fabricated by the microfabrication methods described herein, is bordered by (111) silicon planes after KOH etching. The working electrode 420, defined by the microfabrication methods described above, covers the entire well 450 surface.

In operation, the above embodiments have the advantage of being easy to fabricate and can be fabricated together as a single series microfabrication process step on the substrate. However, successive microfabrication steps may also be employed for fabrication. Furthermore, as the following analysis and experiments below show, these low-cost and easy-to-fabricate biosensors are reusable and have the same robust and reversible electrochemical performance as conventional biosensors.

Figure 6:
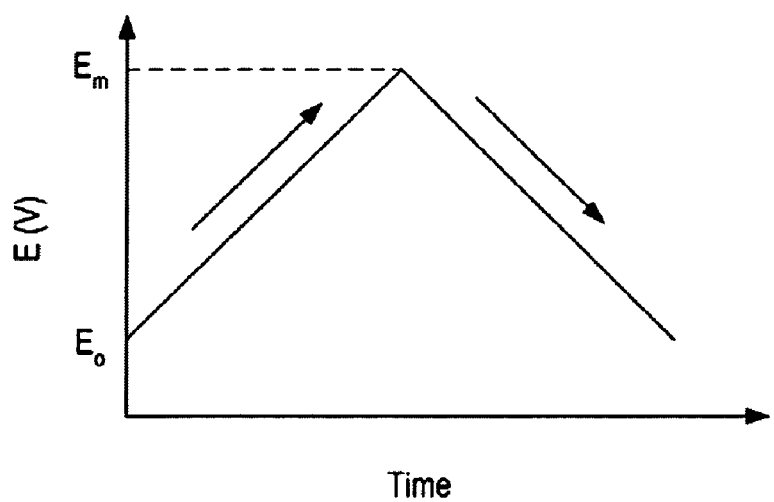
FIG. 6 is a graph of Cyclic Voltammetry (CV) scan potential over time.

In one experiment, Cyclic Voltammetry (CV) analytical technique is used. CV is one of the most versatile analytical techniques used in the study of electroactive species and the characterization of biosensors. It is widely used as both an industrial and academic research tool in the fundamental characterization of electrochemical systems. In Cyclic Voltammetry, the potential is ramped from an initial potential ($E_o$) to a maximum potential ($E_m$) at a controlled (and typically fixed) sweep rate (V/sec). FIG. 6 illustrates this concept. Repeated cycles of reduction and oxidation of the analyte generate alternating anodic and cathodic currents in and out of the working electrode. Since the solution and/or reagent is not stirred, diffusion effects are observed at different analyte concentrations and different scan rates.

Separation of the anodic ($i_{pa}$) and cathodic ($i_{pc}$) current peaks can be used to predict the number of electrons involved in the redox reaction. The peak current is also directly proportional to the analyte concentration, C and scan rate, v. Experimental results are usually plotted as current versus potential, similar to the graph shown in FIG. 7.

Figure 7:
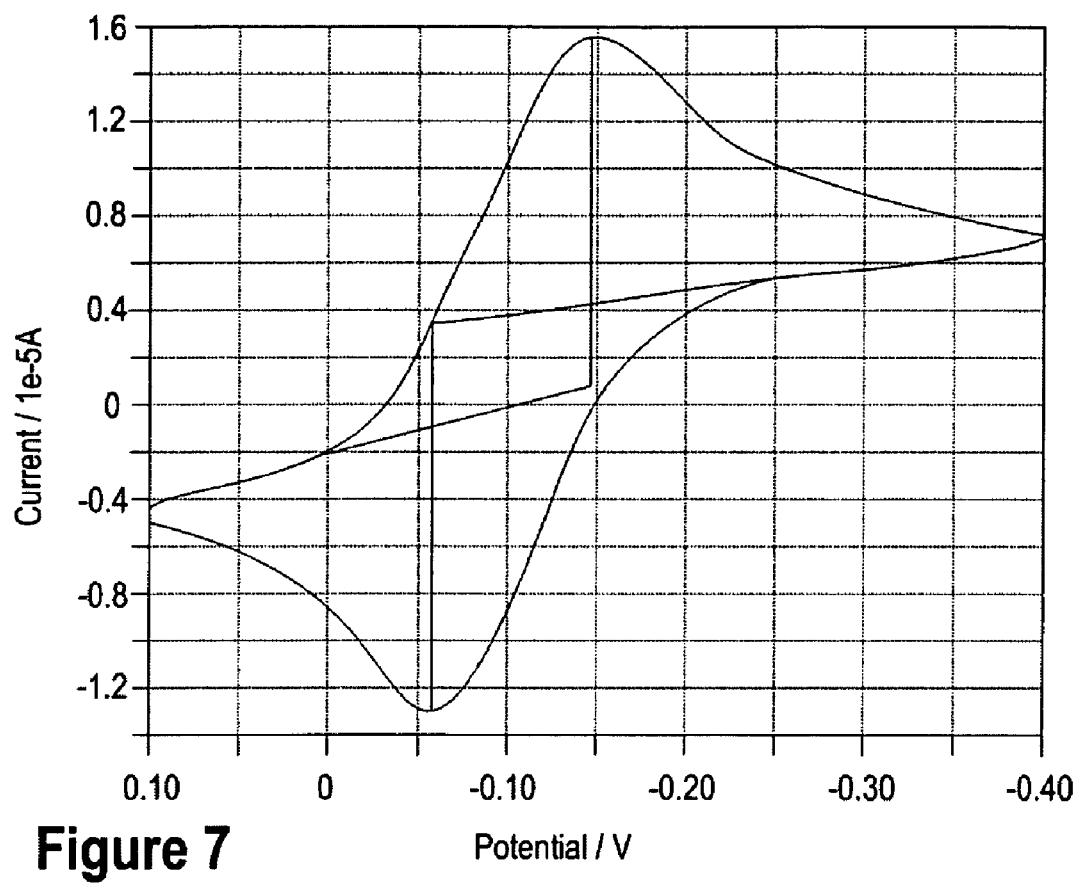
FIG. 7 is a one-cycle Cyclic Voltammetry (current vs. bias potential) taken by a biosensor according to the present invention.

In the CV scan shown in FIG. 7, the potential is graphed along the x-axis with more positive (or oxidizing) potentials plotted to the right, and more negative (or reducing) potentials to the left. The current is plotted on the y-axis with cathodic (i.e., reducing) currents plotted down along the negative direction, and anodic (i.e. oxidizing) currents plotted in the positive direction.

The analyte used in the following control experiment was potassium ferricyanide, $K_3Fe(CN)_6$ (329.26 g/mol), which contains an iron atom in the +3 oxidation state ($Fe^{III}$) in a buffer solution of potassium nitrate, $KNO_3$ (101.11 g/mol). At the surface of a working electrode, a single electron can be added to the ferricyanide anion. This will cause it to be reduced to the ferricyanide anion, $Fe^{II}(CN)_6^{4-}$, which contains an iron atom in the +2 oxidation state ($Fe^{II}$). This simple, one electron exchange between the analyte and the electrode is a well behaved, reversible reaction. This means that the analyte can be easily reduced to $Fe^{II}(CN)_6^{4-}$ and then easily oxidized back to $Fe^{III}(CN)_6^{3-}$.

A redox couple is a pair of analytes differing only in oxidation state. The electrochemical half-reaction for the $Fe^{III}(CN)_6^{3-}/Fe^{II}(CN)_6^{4-}$ redox couple can be written as follows:

$$Fe^{III}(CN)_6^{3-} + e^- \Leftrightarrow Fe^{II}(CN)_6^{4-} \quad E_o 32 + 0.358 V(NHE). \quad (1)$$

Figure 8:
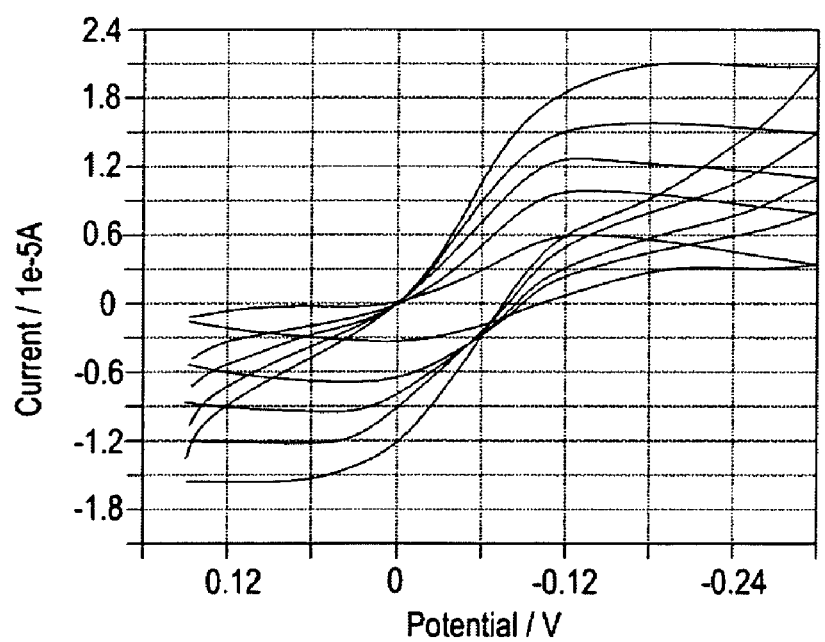
FIG. 8. is a Cyclic Voltammetry (current vs. bias potential) at different scan rate taken by a biosensor according to the present invention.

The voltammogram shown in FIG. 8 exhibits two asymmetric peaks, one cathodic ($i_{pc}$) and the other anodic ($i_{pa}$). Using a standard reference electrode, such as the normal hydrogen electrode (NHE), the formal potential associated with this half-reaction is near +358 mV. If the working electrode is held at a potential more positive than +400 mV, then the analyte tends to be oxidized to the $Fe^{III}(CN)_6^{3-}$ form. This oxidation at the working electrode causes electrons to go into the electrode from the solution resulting in an anodic current. At potentials more negative than +400 mV, the analyte tends to be reduced to $Fe^{III}(CN)_6^{4-}$. This reduction at the working electrode causes electrons to flow out of the electrode into the solution resulting in a cathodic current. Since the preferred sensor design embodiment of the present invention does not utilize a standard reference electrode like NHE, silver/silver chloride (Ag/AgCl) or saturated calomel electrode (SCE), and since all three electrodes are gold (Au), the rest (unbiased) potential in this experiment is close to zero volts.

The important parameters of a cyclic voltammogram are the magnitudes of the cathodic and anodic peak currents ($i_{pc}$ and $i_{pa}$, respectively) and the potentials at which these currents are observed ($E_{pc}$ and $E_{pa}$, respectively). Using these parameters, it is possible to calculate the formal reduction potential ($E_o$—which is centered between $E_{pa}$ and $E_{pc}$) and the number of electrons (n) transferred in the charge transfer reaction.

The peak current ($i_{pa}$ or $i_{pc}$) can be expressed by the Randles-Sevcik equation:

$$i_p = 0.4463 nFAC \left( \frac{nFvD}{RT} \right)^{\frac{1}{2}} \quad (2)$$

where, n=number of electrons appearing in half-reaction for the redox couple
F=Faraday's constant (96,485 C/mol)
A=electrode area (cm$^2$)
v=rate at which the potential is swept (V/sec)
D=analyte's diffusion coefficient (cm$^2$/sec)
R=universal gas constant (8.314 J/mol K)
T=absolute temperature (K)

At 25° C., the Randles-Sevcik equation can be reduced to the following:

$$i_p = (2.687 \times 10^5) n^{3/2} v^{1/2} D^{1/2} AC \quad (3)$$

where the constant has units (i.e., $2.687 \times 10^5$ C mol$^{-1}$ V$^{-1/2}$).

Figure 9:
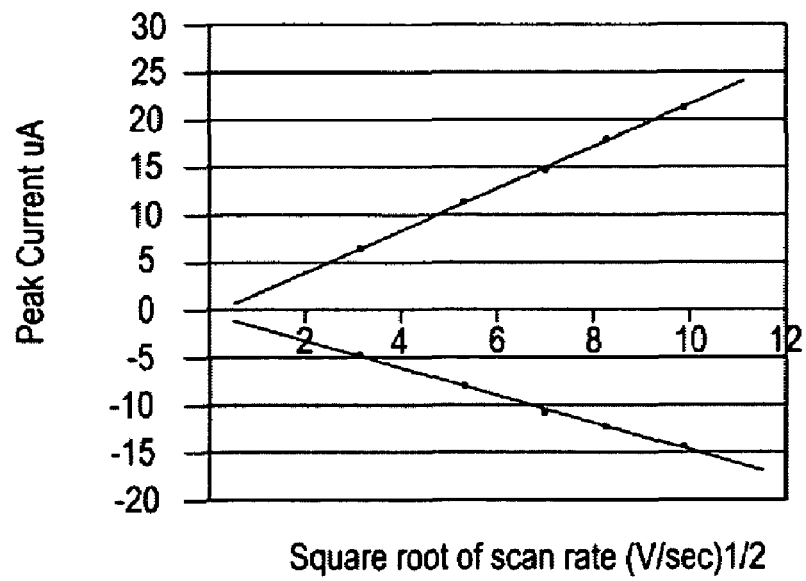
FIG. 9. is a graph of the square root of scan rate vs. peak current taken by a biosensor according to the present invention.

The Randles-Sevcik equation predicts that the peak current should be proportional to the square root of the sweep rate when voltammograms are taken at different scan rates. As shown in FIG. 9, the plot of peak current versus the square root of sweep rate yields a straight line. The Randles-Sevcik equation can be modified to give an expression for the slope of this straight line as follows,

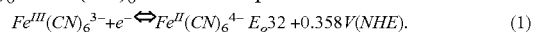

$$\text{Slope} = (2.687 \times 10^{5 \ Cmol^{-1} \ V^{-1/2}}) n^{3/2} D^{1/2} AC \quad (4)$$

Figure 10:
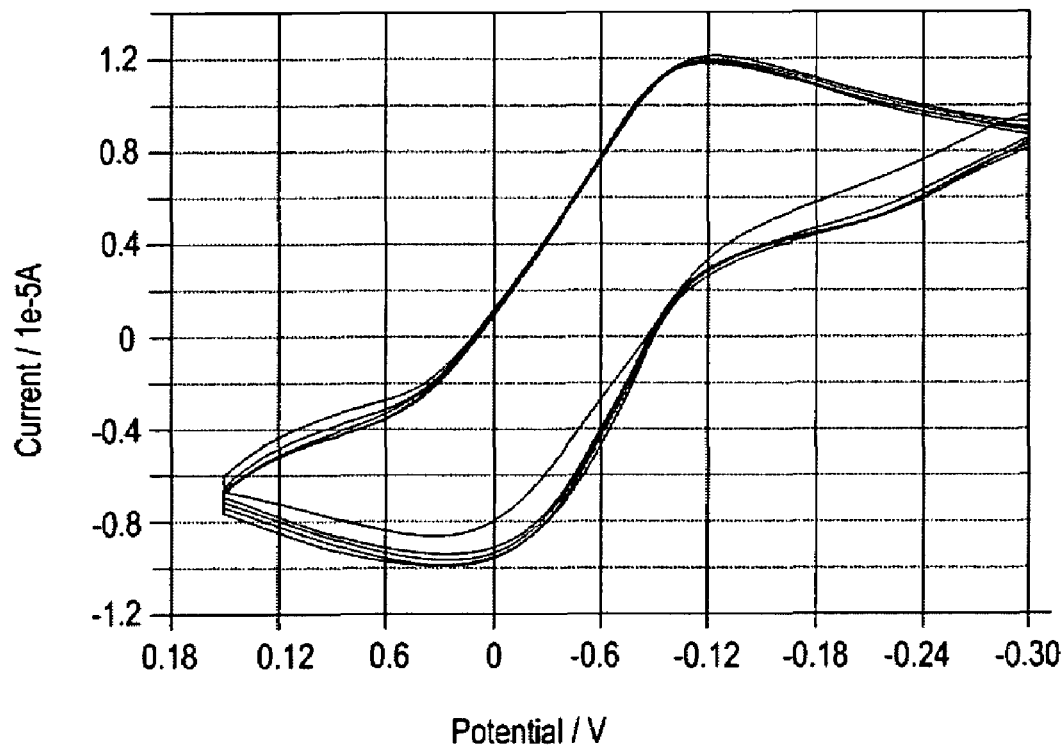
FIG. 10 is a Cyclic Voltammetry (current vs. bias potential) on a plurality of cycles at constant scan rate taken by a biosensor according to the present invention.

The scan rate dependence of the peak potentials and peak currents are used to evaluate the number of electrons participating in the redox reaction as well as provide a qualitative account of the degree of reversibility in the overall reaction. The number of electrons transferred in the electrode reaction (n) for a reversible redox couple is determined from the separation between the peak potentials ($\Delta Ep = Epa - Epc$). For a simple, reversible (fast) redox couple, the ratio of the anodic and cathodic peak currents should be equal to one. The results of the experiment using the preferred sensor design deviate only slightly from unity. Large deviations would indicate interfering chemical reactions coupled to the electrode processes, but slight deviations from unity merely suggest a non-ideal system. FIG. 10 shows the CV scan for 12 consecutive cycles with minor deviations from the first cycle. These results clearly indicate a highly reversible system and robust cell design.

Besides being easy and cheap to fabricate while having the same performance as the conventional sensor, the above embodiments of the present invention also have the advantages of being compatible with the integrated circuit (IC) and the MEMS fabrication process. Furthermore, as shown in FIGS. 3 and 4 these embodiments are capable of being constructed in an array of biosensors and in a small area.

A second aspect of the present invention relates to confinement of a reagent and/or solution in a biosensor using surface tension at small scale. The reagent and/or solution contains the target analyte(s) and/or the chemical(s) needed for biosensing.

A biosensor's performance is mainly determined by its specificity and sensitivity. The concept of confining the reagent on a substrate, such as silicon, was discovered in investigations relating to the present invention to be a solution for reducing the high level of detection noise caused by the non-specific binding of the analyte or other reagent or solution components, such as Horseradish Peroxidase (HRP), onto regions around the periphery of the working electrode and causing high detection noises and creating high false positive rates. HRP is used in the instant embodiment as a signaling enzyme. To verify that noise does come from the HRP residual at the surface, a simple test was done to estimate the contribution of this unwanted binding. HRP was introduced to a bare silicon chip, followed with several wash steps before the addition of the substrate solution. A very high level of enzymatic reaction was observed immediately after adding the substrate solution.

As expected, HRP, like other proteins, sticks to the silicon surface easily and tightly. Several commercial wash solutions and blocking protein were tested without any significant improvement of reducing non-specific binding. It is determined that the best way to avoid the effects of undesirable binding is to prevent it from happening in the first place. The area outside the working electrode of the biosensor of the invention need not encounter the HRP solution in order to achieve biological sensing. In the prior art, however, it is conventional to immerse all three electrodes in aqueous system all the time and all the reagents would flow through all the surface area.

The simplest way, discovered by the present inventive entity, to confine certain reagents within a well-defined space is to form a well in the biosensor. As shown in FIG. 5, a microfabricated well is bordered by silicon crystal planes 400 after KOH etching. The working electrode 420 defined by a lift-off process covers the whole well surface. Thus, a reagent or solution containing components capable of non-specific binding (e.g. HRP) may initially be confined to the well area to achieve the desired binding to the electrode in the well (preferably the working electrode), while avoiding non-specific binding to the periphery region of the biosensor. The reagent or solution can then be washed off the biosensor and additional reagents and/or solutions later added to complete the sensing process.

The importance of surface and material science cannot be underestimated when designing a biosensor. An unacceptable amount of non-specific binding may still occur during the washing process while the diluted reagent is flowing around the wafer surface. The time for the wash solution containing HRP, for example, to stay on the periphery region is much longer than the binding time constant. Therefore, besides fabricating the well structure, the surface of the periphery area preferably should be protected by other mechanisms.

Thus, another way to keep the surface from contacting undesired reagents or binding components is to make it hydrophobic. Silanation of silicon surface is widely used to prevent suspended structures from sticking to substrate by surface tension. This approach was used here to prevent the direct contact of biomolecules to the periphery area of the silicon substrate.

Silane-based molecules with various functional terminal groups have been used to modify surface properties of silicon wafers, silicon nitride chips, and atomic force microscopy (AFM) tips. Silane compounds for the surface modification form robust monolayers chemically tethered to silicon oxide surfaces as a result of hydrolysis of terminal $Si(Cl)_n$ or SiO—$C_2H_5$ groups.

The performance of artificial materials in contact with biological systems is determined by the surface interactions of the two materials. Since the surface interaction could result in noise increasing and structure damage, surface modification is one way to avoid this problem. The easiest way is to change the surface property of the structure or by using plastic. By converting the surface into a biocompatible or bio-inert surface, non-specific interaction will be limited to a minimum or eliminated by the fabrication of a molecular layer firmly tethered to the surface. The most widely implemented approach uses a self-assembly monolayer (SAM) from thiol molecules by chemisorption onto a gold surface and silane molecules to form SAM on a silicon oxide surface according to well-established procedures developed in the 80's mostly by C. D. Bain, and G. M. Whitesides. Other materials such as sol gel and carbon paste may also be used to modify the surface.

In operation, referring now to FIG. 11(a), the reagent is shaped by the hydrophilic working electrode and a droplet is nicely formed over the Au working electrode surface. FIG. 11(b) demonstrates that with increasing volume of the reagent, the area covered by the reagent will gradually expand and then cover the other two electrodes. FIG. 11(c) shows that when an excess stream of reagent is administered by pipette, a ball 465 of reagent will be formed instead of spreading out on the hydrophobic silicon substrate.

Turning now to FIGS. 12 and 13, each individual electrode will be in contact with electrolyte and/or analyte and other components 509 only when needed by using controllable surface property and surface tension force at small scale. Referring now only to FIG. 13, for electrochemical detection, all electrodes have to be immersed in the electrolyte and/or analyte 509 only at detection time. For most applications, the majority of time is spent on sample preparation as depicted in FIG. 12 to immobilize the electrolyte and/or analyte 509 onto working electrode 510. In this embodiment as shown in FIGS. 12 and 13, the coverage of the electrolyte and/or analyte 509 over the electrodes is controlled by surface property and reagent volume 520.

Thus, the above embodiments take advantage of surface tension at small scale to confine the electrolytes and/or analytes and other components. In addition, the above embodiments require much less reagent (in the order of pL to mL); and eliminate the need for bulk solution. Furthermore, because of the small amount of reagent use, the above embodiments have the advantages of having the analyte close to the electrodes (pm to mm), whereby adequate exposure of analyte to the electrodes can be achieved using diffusion effects alone, and the need for stirring or other mixing is eliminated. Another advantage of the above embodiments is the ease of the control and/or change of the coverage of electrolyte and/or analyte over the electrodes. Moreover, the above reagent and/or solution confinement embodiments reduce the loss of target analytes and improve the sensitivity of the biosensor by greatly reduce non-specific binding. In addition, the above embodiments are relatively immune to shaking of the biosensor and are suitable for portable or handheld systems. Lastly, due to the surface tension confinement effect, the reagent will be held firmly by surface tension even the sensor is flipped upside down.

Optionally, as shown in FIGS. 12 and 13, the biosensor embodiments can be equipped with a reaction well 530 to help hold the reagent 520 in place and to control the shape of the reagent 520. However, such a well 530 is not required and the confinement of the reagent 520 can be achieved by a simple flat surface.

Figure 14:
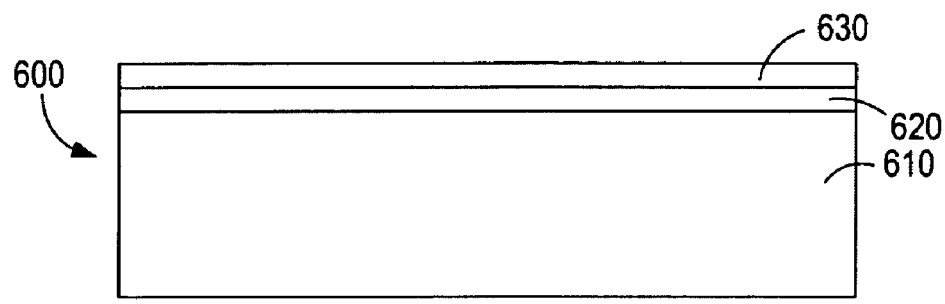
FIG. 14 is a side view diagram showing the first step of how an embodiment of a biosensor of the present invention can be fabricated.

Referring now to FIG. 14, this shows the first step of a preferred fabrication of an embodiment of the present biosensor (sensor-chip). As shown in FIG. 14, a layer of silicon dioxide ($SiO_2$, 1000 Å) 620 is first deposited on a bare Si wafer 610 (prime grade or test grade, p-type or n-type <100>, thickness 500-550 μm). The silicon dioxide 620 serves as a pad layer underneath the silicon nitride 630 ($Si_3N_4$, 1000 Å) to release stress and improve adhesion.

Figure 15:
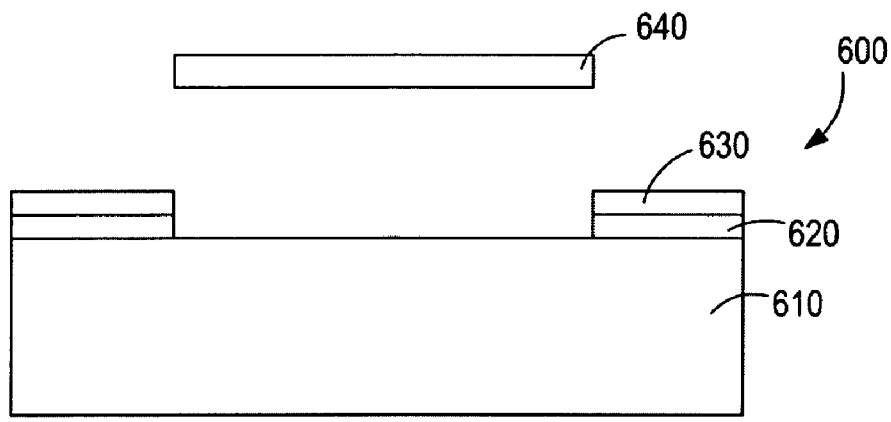
FIG. 15 is a diagram showing the second step of how the biosensor can be fabricated.
Figure 16:
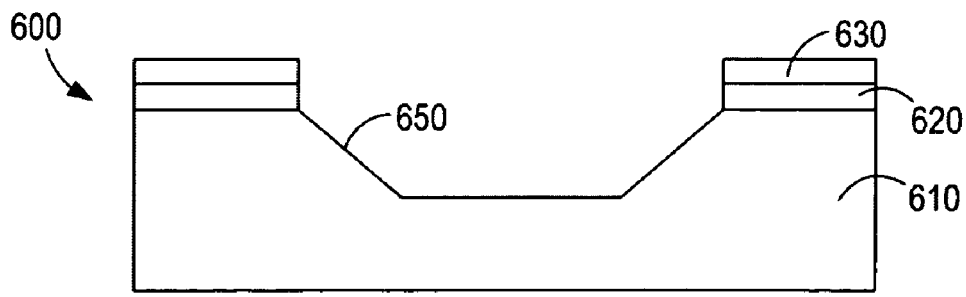
FIG. 16 is a diagram showing the third step of how the biosensor can be fabricated.

Next, referring to FIGS. 15 and 16, the nitride wafer 600 is patterned (FIG. 15) by mask 640 and bulk etched using KOH along the [111] and [100] crystal planes (FIG. 16). The etching creates a well 650 and the depth of the well 650 (up to 350 μm) is controlled by KOH etching time and temperature.

Figure 17:
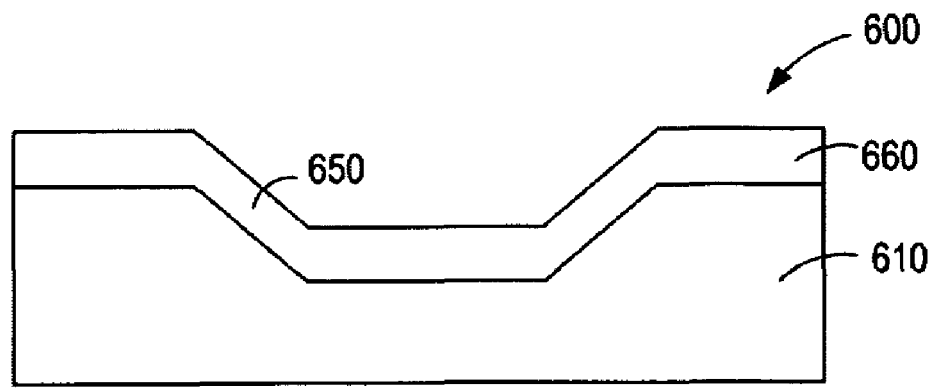
FIG. 17 is a diagram showing the fourth step of how the biosensor can be fabricated.

Referring now to FIG. 17, the nitride 630 and oxide 620 were then removed by HF etching to release internal stress, and another oxide 660 layer (5000 Å) is deposited for electrical isolation.

Figure 18:
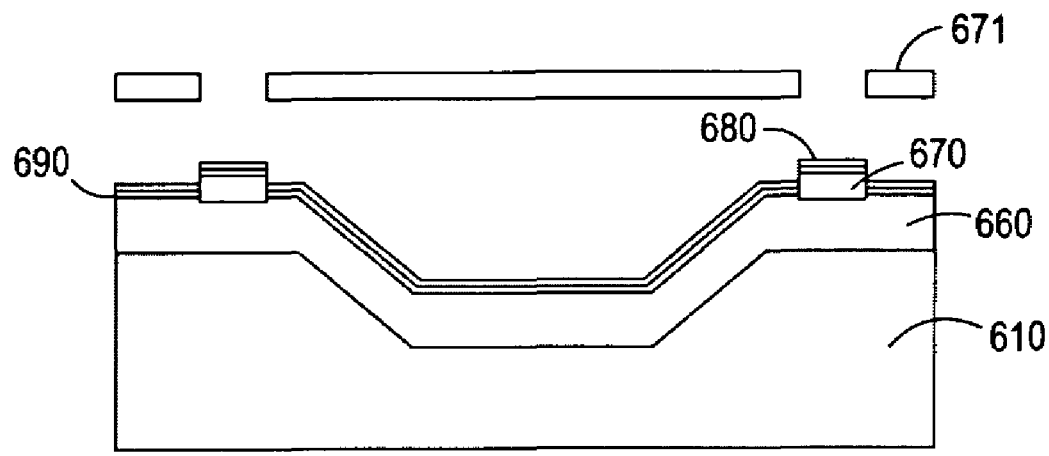
FIG. 18 is a diagram showing the fifth step of how the biosensor can be fabricated.
Figure 19:
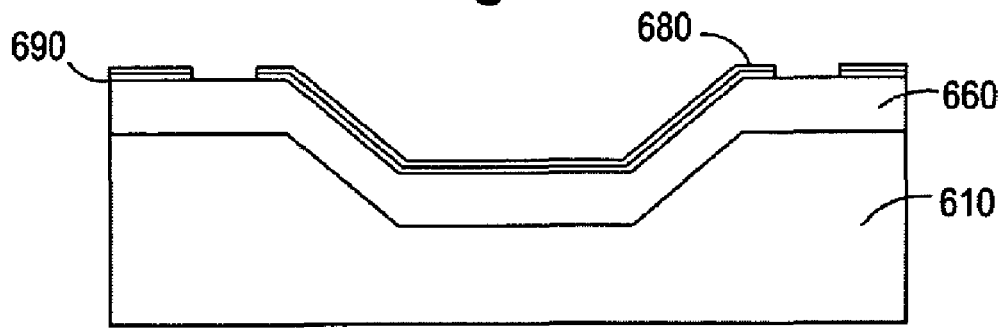
FIG. 19 is a diagram showing the sixth step of how the biosensor can be fabricated.

FIGS. 18 and 19 show a lift-off process for the fabrication of the necessary electrodes. The electrodes for biosensing are patterned on substrate 610 by using PR5214 photo resist layer 670 on silicon dioxide layer 660. Next, a mask 671 is used to transfer a desired pattern onto photo resist layer 670 by using reverse imaging process (which includes the removal unwanted photo resist layer 670). A layer of gold Au (2000 Å) 680 is electron-beam deposited on silicon dioxide layer 660 with the desired photo resist pattern layer 670. Preferably, a deposition of an adhesive 690, such as chromium (Cr 200 Å) occurs before the deposition of Au(2000 Å) 680 to improve the adhesion of the Au onto the silicon dioxide layer 660. In addition, other materials such as titanium or glue may also work as an adhesive. Lastly, referring to FIG. 19, any photo resist 670 and unwanted Au 680 and Cr 690 are removed by dissolving the photo resist pattern layer 670.

Finally the wafer 600 is bathed in hexamethyldisilazane (HMDS) vapor for three minutes after ten minutes of a 150° C. hot bake to generate a hydrophobic surface on the surrounding silicon areas.

Figure 20:
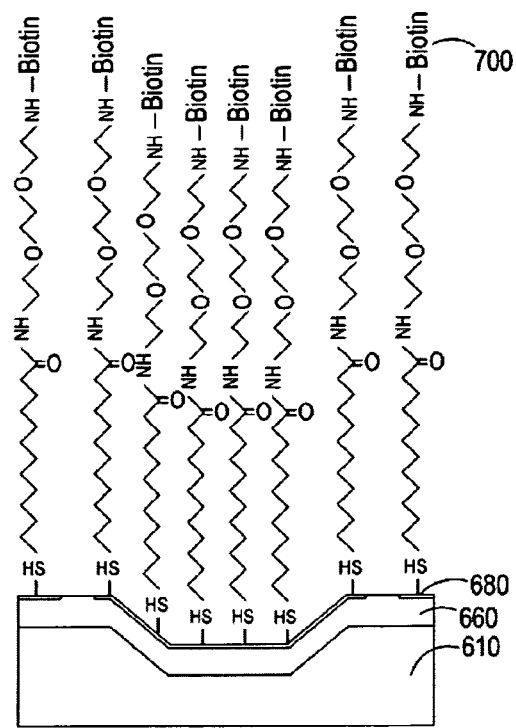
FIG. 20 is a diagram showing how the surface of an embodiment of the present biosensor can be modified to prevent non-specific binding.
Figure 21:
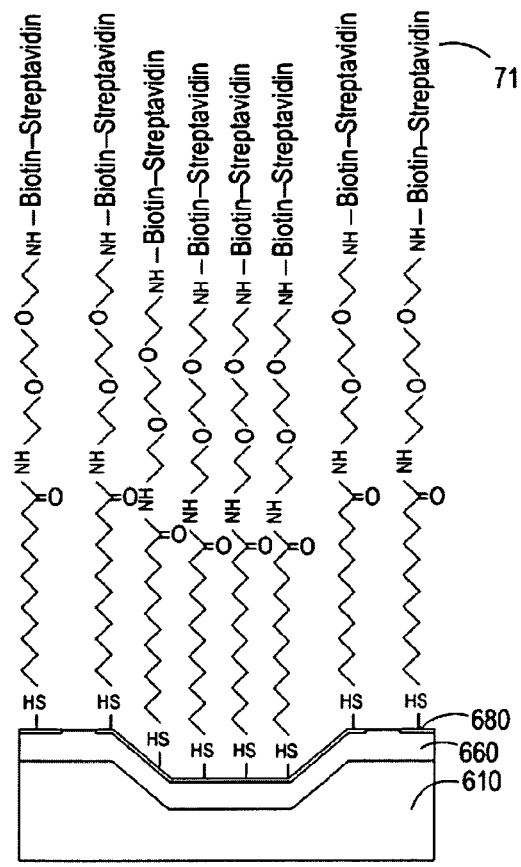
FIG. 21 is a diagram showing the final result on the biosensor surface of the surface modification process in FIG. 20.

Preferably, the surface of the biosensor (sensor chip) is modified by a surface modification step to prevent non-specific binding. As an example, referring to FIG. 20, a macromolecule biosensor's surface can be modified by the steps of first cleaning the Au surfaces 680 with concentrated "Piranha" solution (70 vol % $H_2SO_4$, 30 vol % $H_2O_2$) and thoroughly rinsed with deionized water ($dH_2O$). Next, referring to FIG. 20, surface modification material such as SAM of biotin-DAD-C12-SH (12-mercapto(8-biotinamide-3,6-dioxaoctyl) dodecanamide) Roche GmBH, Germany is deposited. For depositing a SAM of biotin-DAD-C12-SH), the procedure of Spinke, et al. (1993) was used wherein samples were incubated for ~18 hours in a 50 mM solution of biotin-DAD-C12-SH in ethanol with 4.5×10−4M 11-mercapto-1-undecanol (Aldrich Chemical Co., 44,752-8) and rinsed with ethanol and water. Finally, referring to FIG. 21, the biotin-coated Au surfaces 700 were then exposed to a 1.0 mg/ml streptavidin solution for ~10 minutes and rinsed again with $dH_2O$ to form a streptavidin-coated Au surface 710.

A third aspect of the present invention relates to the integration of an entire electrochemical (redox) biosensor onto a single integrated circuit (IC) chip. An integrated circuit (IC) is defined as a tiny wafer of substrate material upon which is etched or imprinted a complex of electronic components and their interconnections.

MEMS devices have distinctive properties as a result of small features but the signal level from MEMS-based sensor is relatively low compared to a conventional sensor. Sensitivity can be improved by using an off-chip amplification module but it also increases the noise and the system size. One embodiment of the present invention includes an on-chip amplification circuitry (amplification circuit incorporated on the biosensor chip itself) and detection circuitry (such as providing bias potential, current measurement, sequential control and signal processing) to reduce the inter-chip interference. Both the detection circuitry and the amplification circuitry can be provided by using bipolar transistor (BJT) and/or complementary metal-oxide-semiconductor (CMOS) devices.

In one embodiment, an on-chip amplification device is equipped underneath the working electrode, which is typically the largest area of the electrochemical sensor cell. Analogous to the open-base bipolar (BJT) photosensor, the base region receives the current from the transducer with the current gain beta β, which ranges from 80-150. There are two types of BJT which can be implemented with an electrochemical cell, vertical BJT and horizontal BJT. The current gain is determined by the length of base region. In vertical BJT, this is a function of ion implementation energy and doping concentration. In horizontal BJT, the length is a function of lithography resolution, ion implementation angle and thermal diffusion. For these reasons the vertical BJT is more reliable in terms of chip-to-chip or in-chip gain uniformity.

Figure 22:
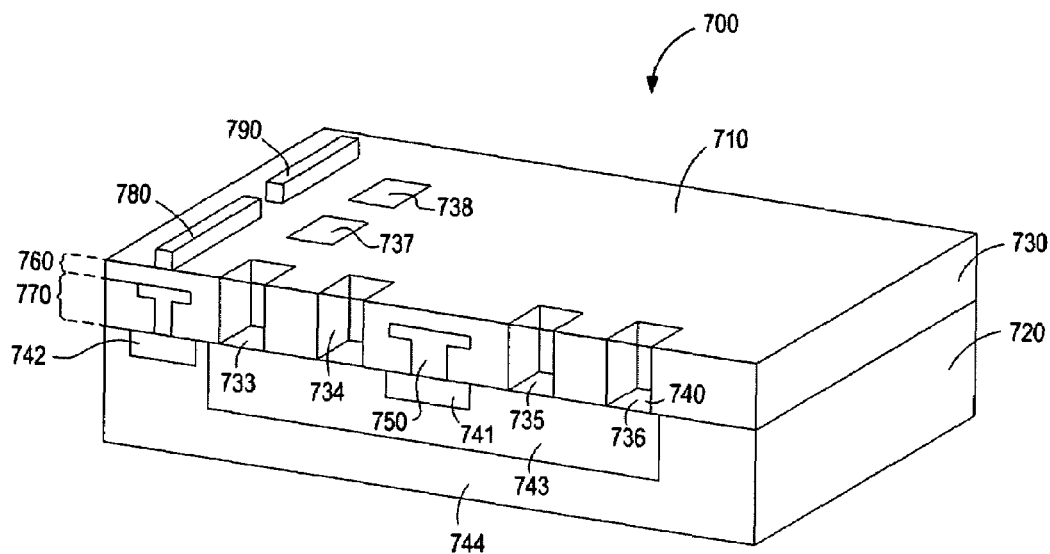
FIG. 22 is a sectional diagram of an embodiment of the present invention of a biosensor system with a biosensor integrated with integrated circuit components.

FIG. 22 shows in cross-section an embodiment of in-chip amplifier circuitry that preferably includes a biosensor comprising three metal electrodes used for electrochemical sensing. Preferably, the three electrodes are fabricated using integrated circuit (IC) processes and have a relatively large area for interconnection and isolation. The entire biosensor chip 700 can be stacked in two stages (electrochemical sensing stage 730 and bipolar transistor (BJT) amplifying stage 720) and the Au working electrode 710 can act as an electromagnetic shield for the BJT device 720. The working electrode contacts (such as contacts 733, 734, 735, 736, 737 and 738) make contact to a contact interface 740 and also increase the surface area of the working electrode 710 for higher signal. All contact and electrode structures can be made with a single layer of metal such as gold. In addition, biosensor chip 700 comprises a silicon substrate 744. Substrate 744 includes a base region 743, a collector 742 and an emitter 741. Base region 743 receives electron flux from working electrode 710. Collector 742 is connected to a power source and provides the current gain under certain base conditions for amplification reasons. A resulting current from base 743 and collector 742 is then measured at emitter 741.

Referring still to FIG. 22, metal interconnect 750 is connected to signal output (not shown) and emitter 741. Gold working electrode 710 connects to base region 743 through a first layer 760 of silicon dioxide via etching. A second layer of silicon dioxide 770 isolates the BJT 720 and signal line while first layer 760 isolates the three electrodes (working electrode 710, reference electrode 780, and counter electrode 790). The contacts (such as contacts 733, 734, 735, 736, 737 and 738) on working electrode 710 increase the surface area and also form a solid contact with BJT 720. The dimension of the contacts (about a few tenths μM each) is much larger than the size of the optional protein SAM (about a few tenths Å) on working electrode 710 so the protein adsorption will not be affected.

Figure 23:
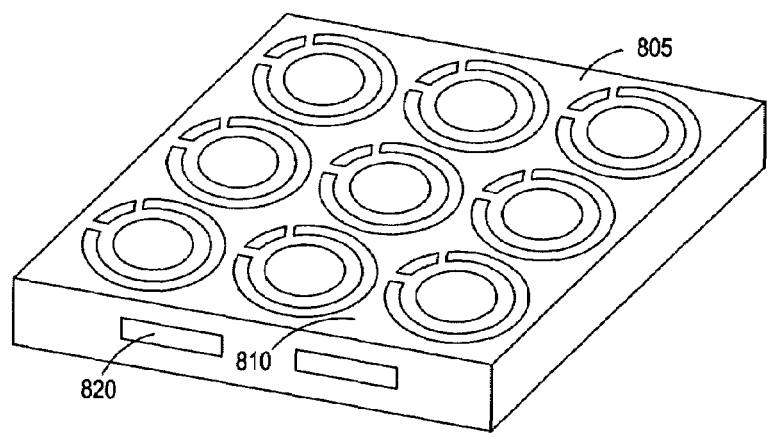
FIG. 23 is a diagram of an embodiment of the present invention of a plurality of biosensors integrated with integrated circuit components.
Figure 24:
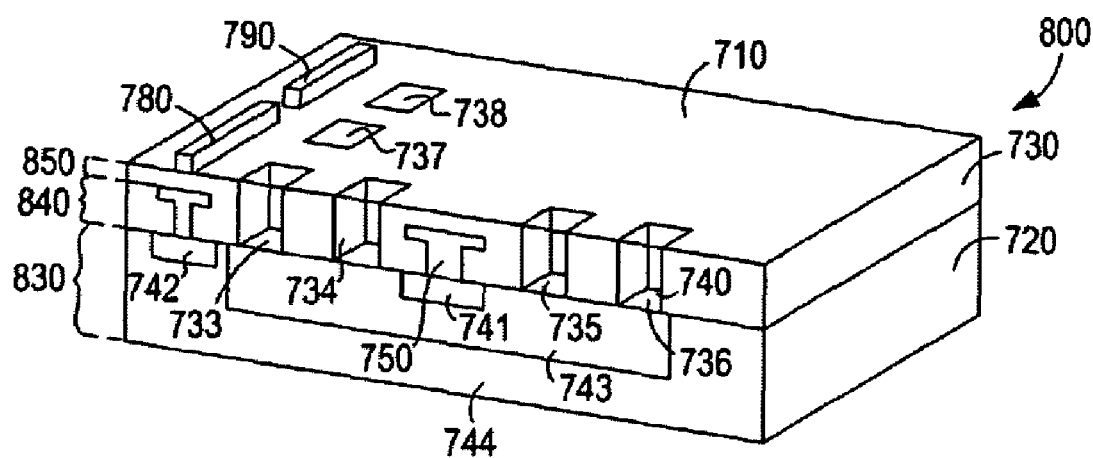
FIG. 24 is a sectional diagram of a biosensor unit that, together with other similar units, makes up the plurality of biosensors integrated with the integrated circuit components in FIG. 24.

FIG. 24 shows a sectional view of another preferred embodiment of a biosensor unit 800 representing a preferred embodiment of a plurality of biosensors 810 positioned on a substrate 805 housing semiconductor components 820 as shown in FIG. 23. As seen in FIG. 24. the biosensor unit 800 comprises a CMOS and/or BJT layer 830, an electrochemical layer 840 and a reagent containment layer 850, and is generally similar to the FIG. 22 embodiment already described.

Thus, as shown in FIGS. 22, 23 and 24, the third aspect of the present invention is related to a biosensing system that allows for direct integration without chip-to-chip connection of the components in the sensor with other components needed for biological detection. The system does not require an external component (instrument) or requires only a minimum number of external components to constitute a complete system. Furthermore, this all-in-one biosensing system reduces the cost and noise level of biological sensing and simplifies the process of such sensing.

Figure 25:
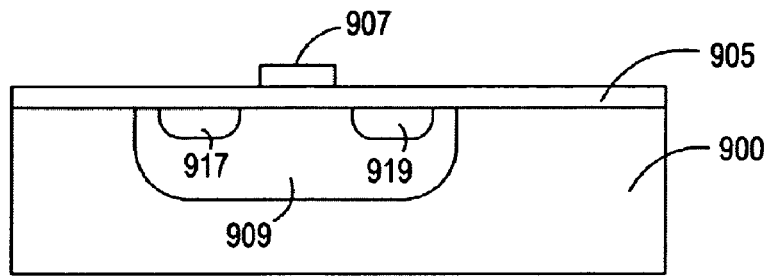
FIG. 25 is a diagram showing the first step of how an embodiment of a biosensor (sensor-chip) of the present invention can be fabricated by integrated circuit (IC) technology with a CMOS device integrated on the biosensor (sensor-chip) itself.

Referring now to FIG. 25, which shows an example of how an embodiment of the present biosensor (sensor-chip) can preferably be fabricated by integrated circuit (IC) technology with a CMOS device and/or devices. In addition, a BJT device and/or devices (not shown) may also be included. As shown in FIG. 25, an integrated circuit (IC) is fabricated on semiconductor substrate 900 with a layer of silicon dioxide 905 with a poly silicon gate 907 on top of a active well region 909. Poly silicon gate 907 is fabricated from an amorphous silicon and it is used for switching the transistor comprises low resistance source 917 and drain 919.

Figure 26:
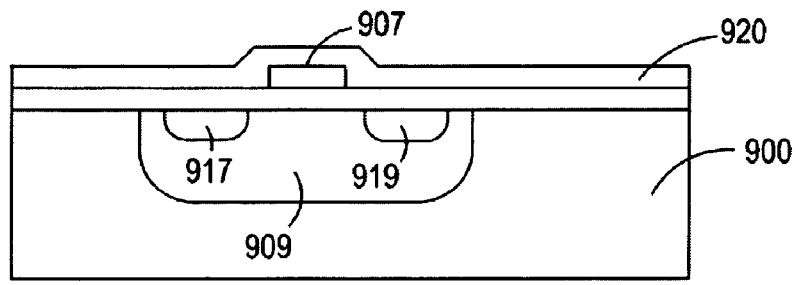
FIG. 26 is a diagram showing the second step of how the biosensor (sensor-chip) can be fabricated by integrated circuit (IC) technology.
Figure 27:
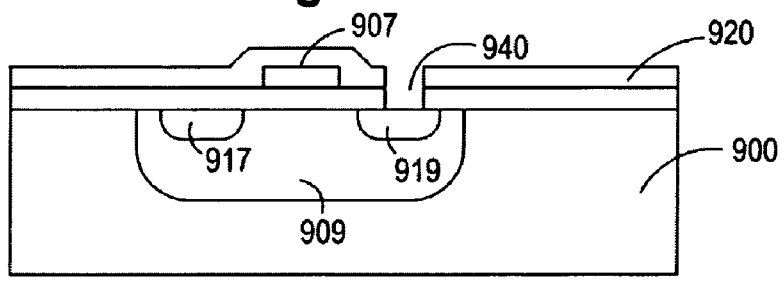
FIG. 27 is a diagram showing the third step of how the biosensor (sensor-chip) can be fabricated by IC technology.
Figure 28:
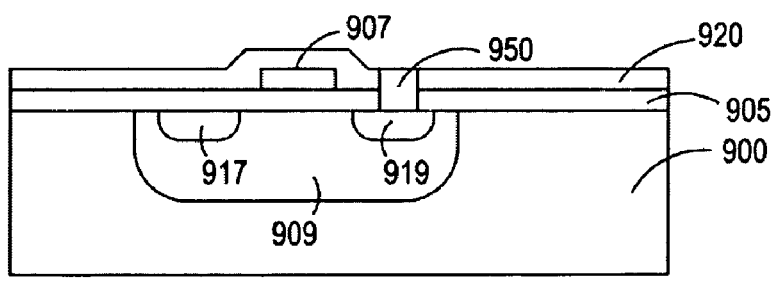
FIG. 28 is a diagram showing the fourth step of how the biosensor (sensor-chip) can be fabricated by IC technology.

Referring now to FIG. 26. a second silicon dioxide layer (5000 .ANG.) 920 is next deposited on the substrate 900 for electrical isolation. Referring now to FIG. 27, the second silicon dioxide layer 920 is then selectively etched by using lithography and etching methods to form an electric connection hole 940. Referring now to FIG. 28, a conducting plug 950 is then applied into the contact hole 940. Conducting plug 950 is used as interconnection between conductive electrode 960 with low resistance source 917 and/or drain 919.

Figure 29:
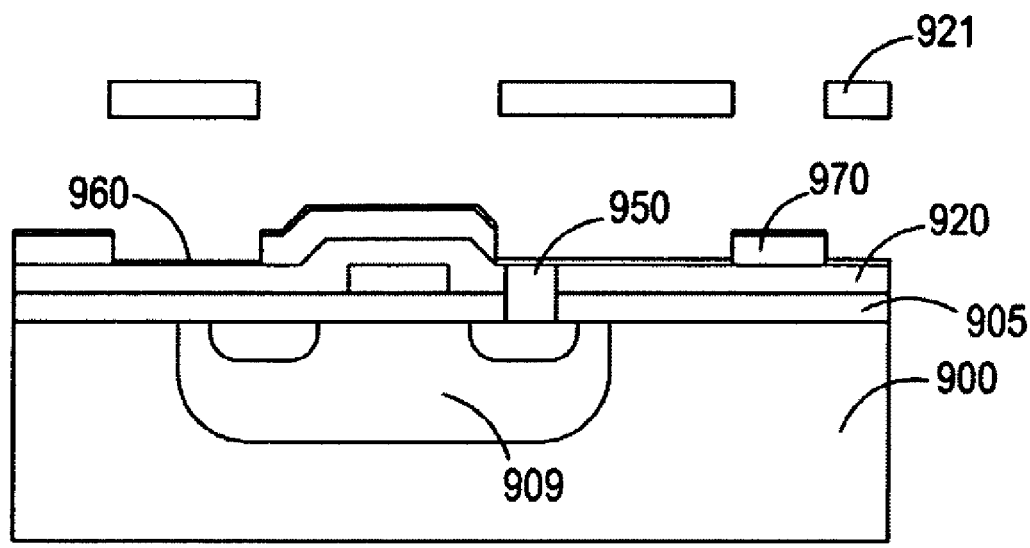
FIG. 29 is a diagram showing the fifth step of how the biosensor (sensor-chip) can be fabricated by IC technology.
Figure 30:
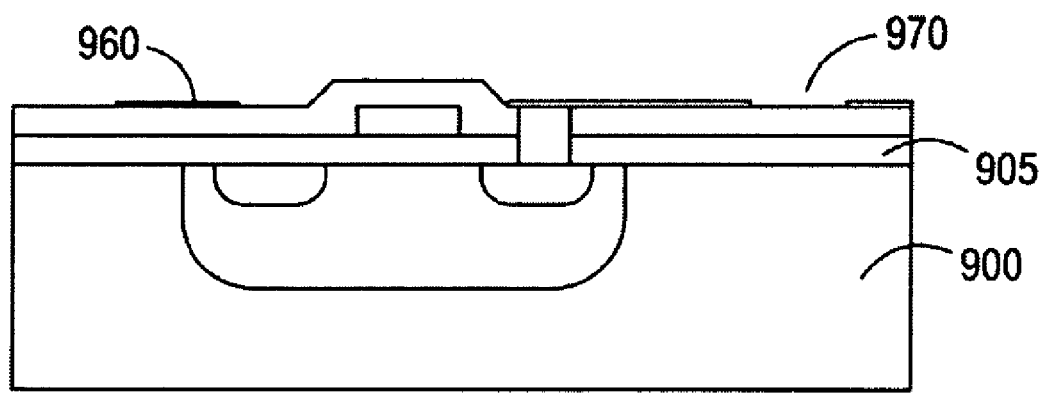
FIG. 30 is a diagram showing the sixth step of how the biosensor (sensor-chip) can be fabricated by IC technology.

FIG. 29 shows a lift-off process for the fabrication of the necessary electrodes. The electrodes for biosensing are patterned on substrate 900 by using PR5214 photo resist layer 970 on the second silicon dioxide layer 920. Next, a mask 921 is used to transfer a desired pattern onto photo resist layer 970 by using reverse imaging process (which includes the removal of unwanted photo resist layer 970). A layer 960 of gold Au(2000 .ANG.) and/or Cr(200 .ANG.) is electron-beam deposited on the second silicon dioxide layer 920 with the desired photo resist pattern layer 970. Lastly, referring to FIG. 30, any photo resist 970 and unwanted Au/Cr 960 are removed by dissolving the photo resist pattern layer 970.

Figure 31:
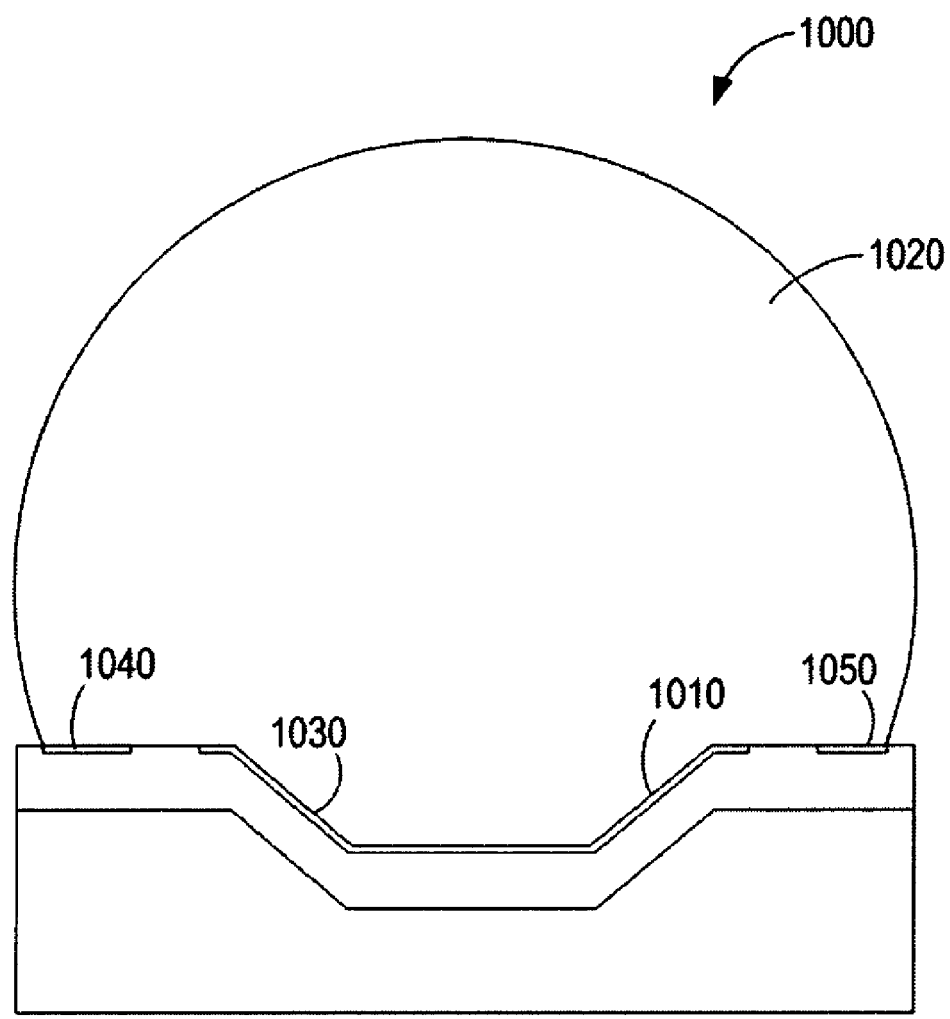
FIG. 31 is a diagram showing how an embodiment of a biosensor of the present invention can be use to detect ionic analytes (or molecules).

Referring now to FIG. 31, this shows an example of how an embodiment of the present biosensor (sensor-chip) 1000 can preferably be used to detect an ionic molecule, such as iron (Fe). In this embodiment, the sensor surface 1010 is not modified and is ready to use after the post fabrication cleaning as shown in the above fabrication embodiment. The analyte used in this embodiment was potassium ferricyanide, $K_3Fe(CN)_6$ (329.26 g/mol), which contains an iron atom in the +3 oxidation state ($Fe^{III}$) in a buffer solution of potassium nitrate, $KNO_3$ (101.11 g/mol). As shown, in FIG. 31, the mixed solution 1020 with analytes (or reagent with electrolytes) is applied onto all three electrodes (working 1030, reference 1040 and counter electrode 1050). The volume of the solution 1020 is adjusted so the droplet is confined over all three electrodes by surface tension forces.

Figure 32:
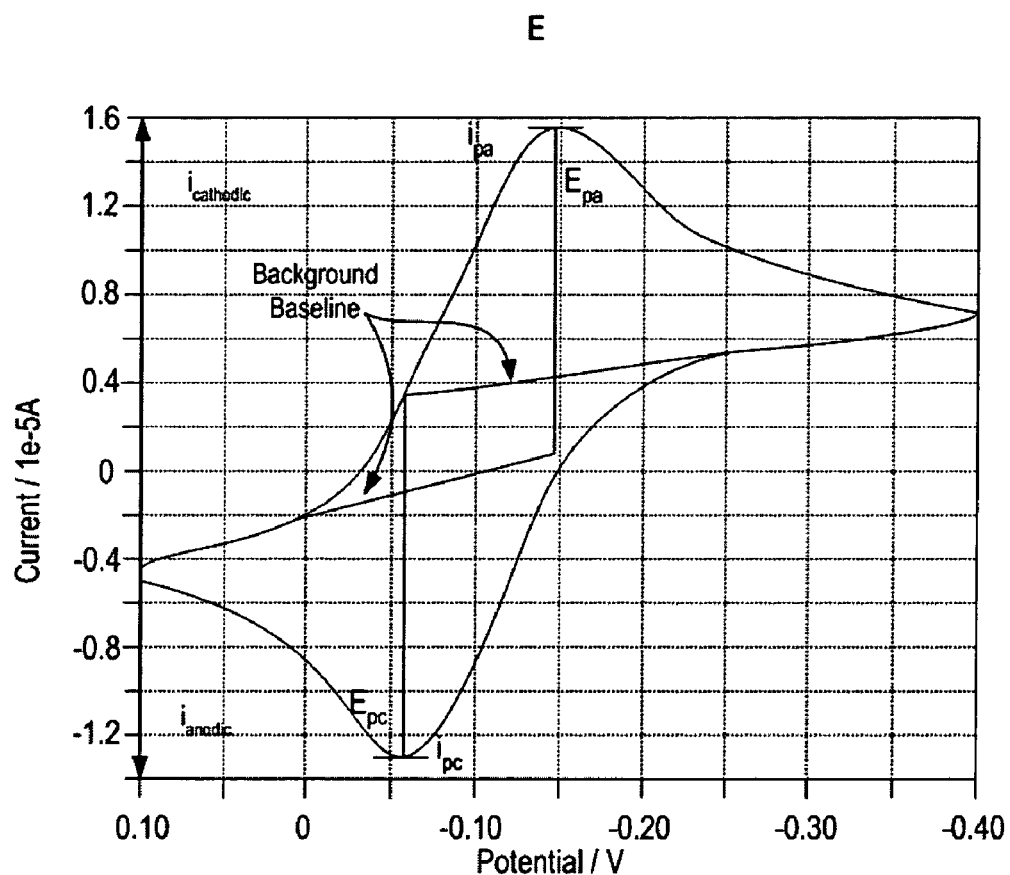
FIG. 32 is Cyclic Voltammetry (CV) (current vs. bias potential) graph taken by the sensor of FIG. 31.

Next, referring to FIG. 32, the Cyclic Voltammetry (CV) current vs. bias potential was measured using a CH Instruments 660A Electrochemical Workstation with a picoamp booster and faraday cage. The potential is swept between 0.1 volt and −0.4 volt and the current is measured through working electrode 1030.

After the measurement, the Au surfaces were cleaned with acetone, alcohol, and concentrated "Piranha" solution (70 vol % $H_2SO_4$, 30 vol % $H_2O_2$) and thoroughly rinsed with deionized water ($dH_2O$) if the sensor 1000 is to be re-used.

Figure 33:
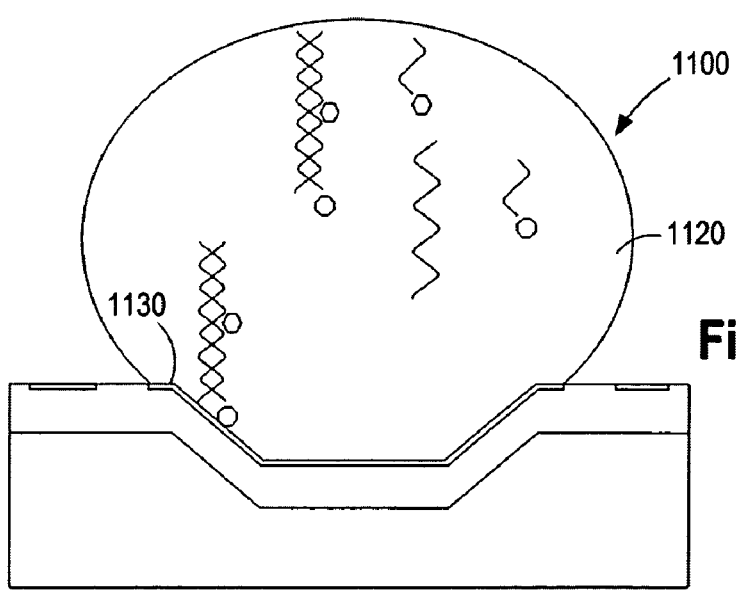
FIG. 33 is a diagram showing the first step of how an embodiment of a biosensor of the present invention can be used to detect macromolecules (e.g. DNS, RNA, protein).

FIG. 33 shows a preferred embodiment for macromolecules (e.g., DNA, RNA, protein) detection. Preferably, the detection of the concentration of macromolecules (DNA, RNA, protein) does include the sensor surface modification of biotin/Streptavidin layer. The sensor surface is modified with a proper biochemical solution to form a streptavidin layer after the post-fabrication cleaning as shown in the surface modification process described above. After the surface of the biosensor 1100 has been modified, the amperometric biosensing of pathogen is conducted by first adding 50 ml of lysis reagent (0.4 M NaOH) to a 250 ml sample of bacteria solution and incubated for 5 minute at room temperature. 100 ml of probe solution (anchoring and signaling probes) was then added, and the mixture was incubated for 10 min. at 65° C. 5 μL of the lysed *E. coli*/probe solution mixture 1120 is then placed on the streptavidin coated working electrode 1130 of the biosensor 1100 and incubated for 10 min. at room temperature.

Figure 34:
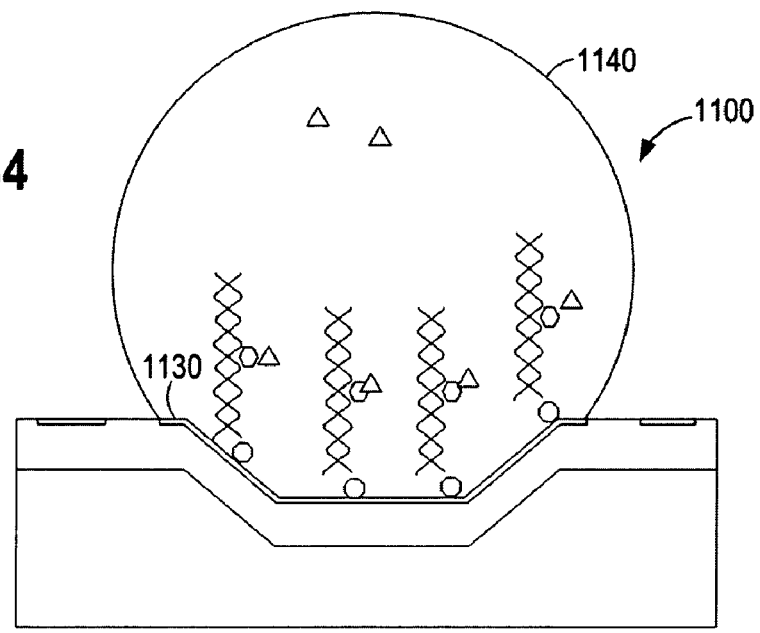
FIG. 34 is a diagram showing the second step of the detection of the macromolecules.

Referring now to FIG. 34, the biosensor 1100 is then washed with biotin wash solution (Kirkegaard and Perry Laboratories, 50-63-06). Next, 5 μL 1140 of Anti-F1-POD (Anti-fluorescein peroxidase, 150 U, Roche Inc., 1 426 346), diluted to 0.75 U/ml or 0.15 U/ml with dilutant (PBS/ 0.5%Casein) is placed on the working electrode 1130 and incubated for 10 minutes at room temperature.

Figure 35:
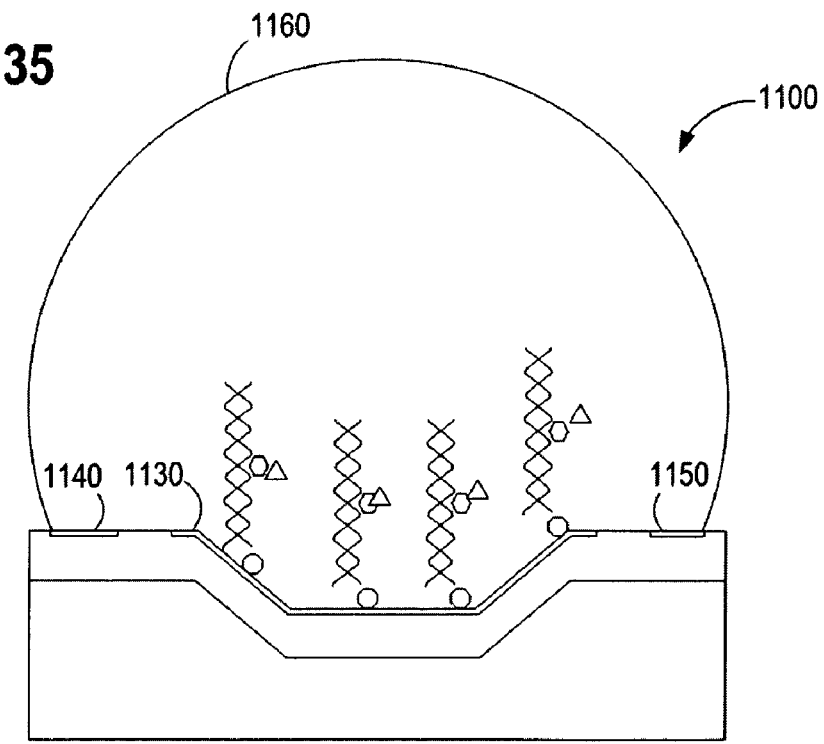
FIG. 35 is a diagram showing the third step of the detection of the macromolecules.

Referring now to FIG. 35, the biosensor is then washed again with wash solution. After the wash, 10 μL 1160 of K-blue substrate (Neogen Corp., 300176) is placed on the biosensor in such a way that all three electrodes (working 1130, reference 1140, counter 1150) are covered by the substrate solution 1160.

Finally, the electrochemical (more specifically the redox) measurements are immediately taken. Amperometric current vs. time is measured using a CH Instruments 660A Electrochemical Workstation with a picoamp booster and faraday cage. Samples on the biosensor are to be measured sequentially. The voltage should be fixed at −0.1V (vs. reference), and a cathodic current (amperometric signal) reading should be taken in 20 seconds because at 20 seconds, the current values should reach steady-state. Cell concentration (cell number) is determined by using serial dilutions and culture plate counting.

After the measurement, the Au surfaces should then be cleaned with acetone, alcohol, and concentrated "Piranha" solution (70 vol % $H_2SO_4$, 30 vol% $H_2O_2$) and thoroughly rinsed with deionized water ($dH_2O$) if the sensor 1100 is to be re-used.

Preferably, in any of the above biosensor embodiments the biosensor is calibrated before actual sample detection. The biosensor is preferably calibrated with a calibrating solution that contain a known amount of target analyte(s) and another calibrating solution that contains an undetectable amount (e.g., none) of the target analyte(s). Optionally, the biosensor may be calibrated with a plurality of calibrating solutions. Each of the plurality of calibrating solutions respectively contains a known amount of the target analyte. Preferably, the calibrating solutions contain the target analytes at different level of concentrations. These calibrations solutions are measured on the biosensor by the above described detection process to obtain a reference signal and/or reference signals. The reference signal and/or signals are then compared with the measured signal from a sample solution to determine the presence and quantity of the analyte in the sample reagent. The determination of the presence and quantity (e.g., concentration or absolute amount) of the analyte(s) can be determined by conventional biological interpolation methods.

Enzyme-Based Electrochemical Biosensor with DNA Array Chip

A reusable DNA sensor array for rapid biological agent detection has been fabricated on a silicon chip. The DNA-based probes target the DNA/RNA sequence of the analyte instead of indirect probing using antibodies. The sensitivity is greatly enhanced by combining the hybridization event with a signal enzyme. The formation of the self-assembled monolayer sensor surface, in-situ DNA hybridization, signal measuring and the sensor regeneration can be performed within 40 minutes. Even without using the PCR, as low as 1000 Escherichia coli (E. coli) cells through 16s rRNA can be detected using this sensor array. (FIG. 36) The dimension of each sensor area ranges from 25 mm$^2$ to 160 µm$^2$.

Figure 36:
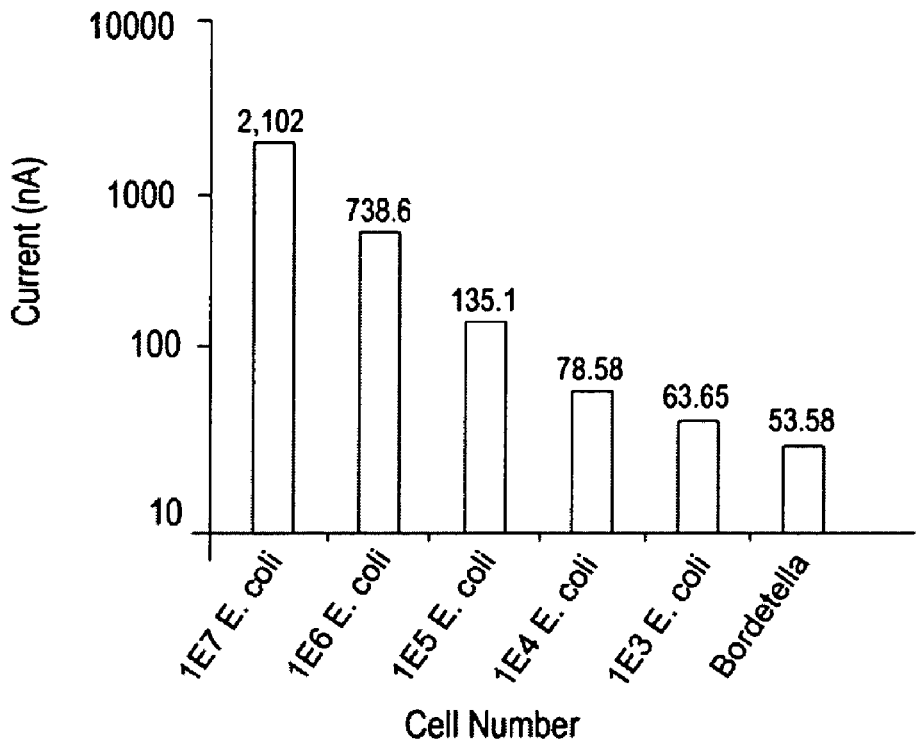
FIG. 36 is a graph on sensitivity and specificity check.

The enzyme-based electrochemical biosensor is primarily motivated by the need for a highly sensitive and selective protocol capable of rapid monitoring the concentration of bacteria, virus, or various biological species for field use. Such a protocol would operate remotely, and would be fully automated, compact, and robust. Therefore, the electrochemical transducer with minimum power consumption and smaller size is preferred over the optical system. High specificity can be achieved by using DNA hybridization to reduce false positive and false negative signals. DNA electrochemical biosensors have been previously reported using graphite or carbon electrodes. Carbon-based electrodes, however, are generally not adaptable to MEMS technology when small (<µm) dimensions are needed. In this study, Au is used as electrodes, with a protein self-assembled monolayer (SAM) to capture the E. coli rRNA. An enzyme is used as a biological amplifier in this study to gain the high sensitivity without PCR. A sensitivity and specificity check for E. coli MC4100 versus Bordetella SB54 is shown in FIG. 36.

Figure 37:
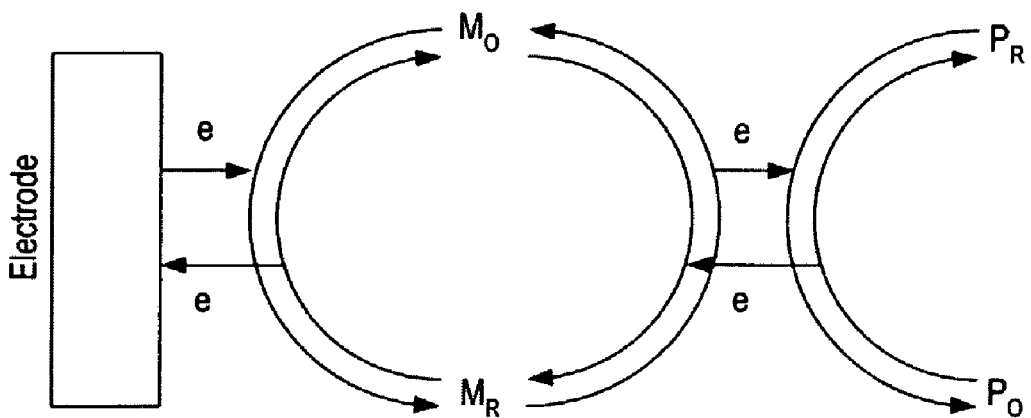
FIG. 37 is a diagram showing the electron transport of HRP enzymatic reaction.

HRP is one of the most widely used enzymes for analytical purposes and biosensors application. Enzymatic amplification occurs due to a high turnover number in reactions that can be detected electrochemically. An amperometric biosensor based on horseradish peroxidase (HRP) with 3,3'5,5'-tetramethylbenzidine (TMB) as a mediator is described (FIG. 37). The electron transfer at the electrode surface is measured amperometrically to represent the number of the enzymes immobilized by DNA hybridization though the 16s ribosomal RNA of the target cell. Therefore, the output current is proportional to the number of the target cells in the solution.

A three-electrode electrochemical cell is constructed with a micro-fabricated reaction well for the working electrode. Gold (Au) is deposited as a conducting layer and $Si_3N_4/SiO_2$ as an isolation layer. The surrounding Si surface is modified to be hydrophobic. The three dimensional reaction well along with the hydrophobic nature of the surrounding area allows a liquid droplet to be well contained in the working electrode. This design minimizes non-specific binding of biomolecules to other areas of the sensor chip. The Au working electrode has a monolayer of streptavidin immobilized on the surface via a thiolated-biotin SAM or through direct protein adsorption onto the gold. A sample solution containing E. coli is treated with lysis buffer, the target DNA/RNA from the E. coli cells are hybridized with both an anchoring ssDNA probe and a labelling ssDNA probe at annealing temperature (~65° C.) in the presence of cell debris. The anchoring probe (conjugated to biotin) and the labelling probe (conjugated to fluorescein) recognize two distinct conservative sequences; therefore, the hybrid forms only with the specific gene segment from the target bio-agent. The oligonucleic hybrid is then immobilized through biotin-streptavidin binding onto the working electrode and unbound components are washed away. A HRP-linked anti-fluorescein antibody is then loaded onto each hybrid. After addition of substrate, enzymatic reaction causes a current signal which is measured amperometrically using the three-electrode cell. The entire protocol is completed in 40 minutes.

Figure 38:
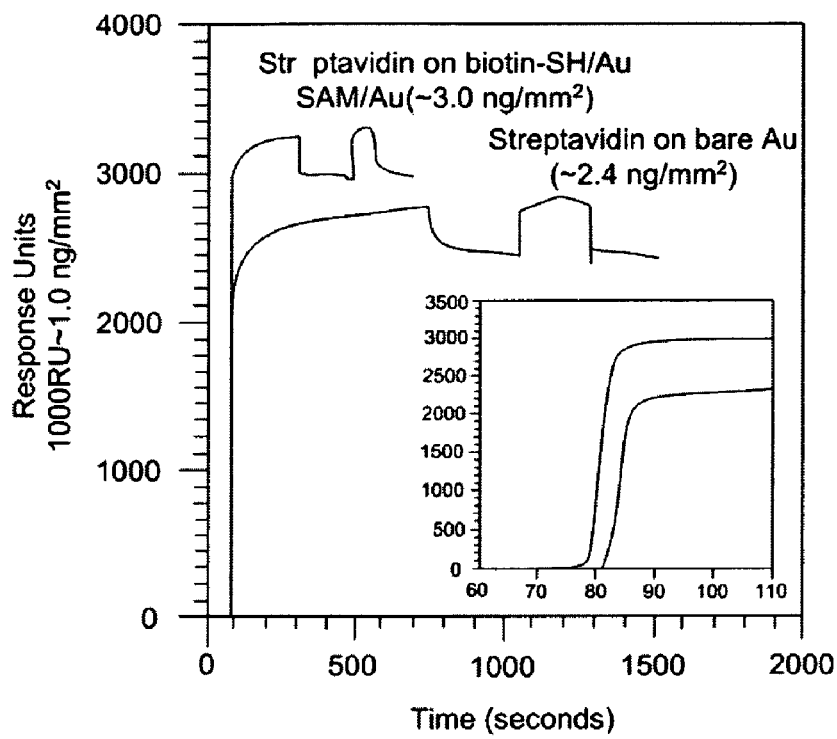
FIG. 38 is a graph on the Surface Plasmon Resonance of Streptavidin on Biotin-SH/Au or Bare Au.

The SAMs on the DNA sensor were characterized by surface plasmon resonance (SPR) and atomic force microscopy (AFM) to determine whether only a monolayer was deposited and also to determine the kinetics of protein deposition. From this data, the time scale required for in situ sensor surface formation in the integrated fluidic system can be ascertained. Two different methods were used to deposit the streptavidin SAM; one using a thiolated biotin and the other using direct protein adsorption. In both cases, SPR data shows that only one monolayer was deposited on the surface (FIG. 38). A crystalline monolayer of streptavidin has an expected surface coverage of 2.8 ng/mm$^2$. The results indicate that a full monolayer was obtained using the thiolated biotin and ~80% coverage was obtained by direct protein absorption. Moreover, protein binding/adsorption occurs within ~10 seconds.

Atomic Force Microscopy (AFM) was performed in the contact mode using ultralever tips with a force of 5.0 nN. The Au substrate was prepared following Wagner method. The bare Au has topographic features <10 Å, and contact AFM of a "full" monolayer showed a smooth surface with evidence of protein dragging. The height of protein islands on a "partial" monolayer was ~45 Å, consistent with the dimensions of the streptavidin protein. The AFM observations confirm the SPR results that only one monolayer was deposited.

In summary, the combination of MEMS technology with established DNA technology leads to a highly specific and sensitive detector for pathogenic bacteria. Biological identification using electrochemical detection with SAMs was successfully incorporated into a silicon wafer with a sensitivity that can detect less than 1,000 E. coli cells.

Optimization of DNA Microsensor Arrays for Biological Detection

The characterization and optimization of a reusable DNA microsensor array for rapid biological agent detection is described in the following. This MEMS based DNA sensor utilizes a standard three-electrode electrochemical cell configuration with novel micro fabricated structure design to minimize non-specific binding. The sensor module is easily adapted to various protocols and can be used for rapid detection of macromolecules (DNA, RNA) from targets such as uropathogenic Escherichia coli (E. coli) in urine and microorganisms causing otitis media (middle ear infection). Less than 10$^5$ E. coli cells can be detected from the urine sample of a patient with urinary tract infection. The sensitivity is enhanced by appropriate sensor characterization and surface modification. The total detection time including sample preparation can be reduced to 25 minutes by using a POD conjugated oligonucleotide.

Conventional electrochemical detection is not quite compatible with MEMS technology and fabrication processes due to system requirements and configuration. An electrochemical cell must consist of at least two electrodes (working electrode, reference electrode) and an electrolyte. An electrochemical electrode is an interface at which the mechanism of charge transfer changes between electronic transport and ionic transport. [4] An electrolyte is a medium through which charge transfer can take place by the movement of ions. Electrochemical detection requires a second unvarying potential supplied by a reference electrode, forming a half battery. A typical reference electrode is Ag/AgCl. Currently, it is difficult to fabricate this reference electrode on a silicon substrate. Most MEMS based electrochemical sensors focus on micro fabrication of only the working electrode. The characteristics and application of a MEMS based electrochemical sensor on silicon fabricated by standard MEMS processes are described. Testing of clinical urine samples with DNA hybridization on the electrochemical sensor demonstrates that MEMS based sensor on silicon can be used for biomedical detection.

Nucleic acid molecules (RNA/DNA) from chemically disrupted target cells are hybridized with both an anchoring ssDNA probe (conjugated to biotin) and a labeling ssDNA probe (conjugated to fluorescein) in the presence of cell debris. These two probes recognize two distinct conservative sequences; therefore, the hybrid forms only with the specific genetic segment from the target bio-agent. The oligonucleic hybrid is then immobilized through biotin-streptavidin binding onto the working electrode and unbound components are washed away. A peroxidase (POD)-linked anti-fluorescein antibody is then loaded onto each hybrid. After addition of substrate with a mediator (tetramethylbenzidine, TMB), enzymatic reaction causes a current signal which is measured amperometrically from the REDOX reaction. The entire protocol can be completed in 40 minutes and the sensor is reactivated after a cleaning process.

Most biosensor chips utilize off-chip optical detection. One embodiment of the present invention includes on-chip electrochemical detection with sensor optimization and surface modification for signal-noise-ratio improvement. MEMS technology makes possible the development of miniaturized electrochemical cells since conductive metallic electrodes in small dimensions can be accurately deposited and patterned on a silicon substrate. Au was a suitable candidate for all three electrodes (working, auxiliary, and reference), and characterization of the Au/Au/Au electrode cell using a well-known one-electron system such as ferrocene confirmed that classic reversible one-electron transfer was obtained.

Cyclic voltammetry for reversible one-electron transfer of ferrocene is characterized by a peak separation of ~57 mV between the anodic and cathodic peaks, the same peak maximum, and a linear relationship between peak current vs. [scan rate]$^{1/2}$. Voltammograms of ferrocene using MEMS based electrochemical sensor at different scan rates show the expected behavior and a plot of the peak current at peak maximum vs. [scan rate]$^{1/2}$ is linear. Further characterization of the electrochemical cell using peroxidase confirmed that enzymatic amperometry is also feasible. Cyclic voltammetry conducted on the mediator shows a two-electron redox transfer, as expected for TMB, and addition of the peroxidase enzyme results in an increase in the reduction current that can be clearly measured at −0.1 V bias potential.

The sensor surface has a protein self-assembled monolayer to capture the target RNA/DNA onto the working electrode, and the SAMs have been characterized by atomic force microscopy (AFM) and surface plasmon resonance (SPR). The signal-to-noise can be improved significantly by appropriate surface modifications to reduce non-specific binding. The first approach is to introduce a surface blocking protein to eliminate potential bonding sites for non-specific binding. The second approach is adding a hydrophobic modification of the periphery region with silanation treatment or thin-film coatings of Teflon® or polyimide. With the hydrophilic nature of protein-covered Au working electrode, reagents will be confined to the working electrode only, minimizing deposition of enzyme to the periphery and other two electrodes. In both cases, noise due to non-specific binding was reduced. Typically, the second approach (hydrophobic modification) is used in MEMS fabrication and the first one is incorporated into probe reagent.

Sample preparation is the most time consuming step for most biosensors. Any additional protocol steps will require more fluidic devices and a longer detection time. A simplified protocol whereby the step of the enzyme loading with POD conjugation onto detector DNA probe is eliminated. The hybridization condition was controlled to retain the enzymatic activity of POD after heating to 65° C. The protocol can then be shortened from 40 to 25 minutes while reducing the required number of reagents by one.

Figure 39:
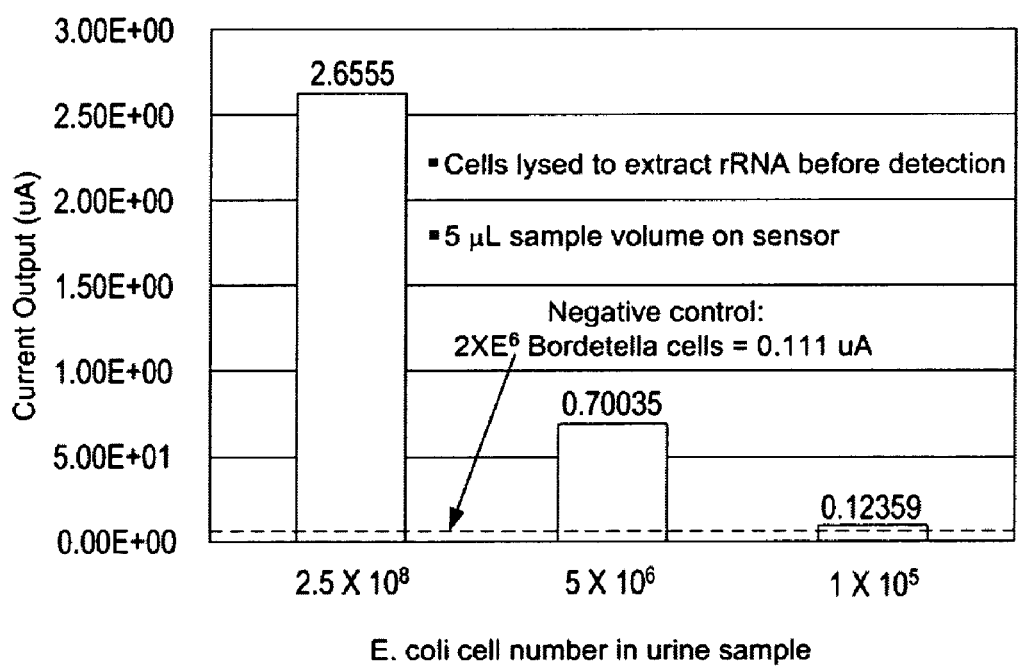
FIG. 39 is a graph on the sensitivity check of micro DNA sensor with urine sample.

Previous work has demonstrated the sensitivity of micro DNA sensor to be ~$10^3$ E. coli cells. Recent data show it has the capability to detect less than 10 E. coli cells from cell culture at stationary stage through ribosomal RNA content. The sensor was then subjected to clinical urine sample from Division of Infectious Disease at UCLA for testing. As shown in FIG. 39, the minimum detectable cell number of E. coli in urine sample is $10^5$ from the preliminary result without isolation. Sensitivity with urine sample can be improved with further optimization. Another type of bacteria, Bordetella, was used as a negative control and all E. coli samples, including dilutions, have higher signal than the negative control.

Micro DNA sensor can be used for electrochemical detection without utilizing a conventional reference electrode because the bias potential is reasonable low (−0.1V), and the detection is short enough (20 seconds) to avoid the accumulation of charge at auxiliary electrode. This was confirmed with voltammograms of ferrocene and POD solution.

Micro DNA sensor can be used for electrochemical detection of pathogens such as E. coli. The Au/Au/Au three-electrode cells patterned on silicon by MEMS technology were successfully used in amperometric measurement of enzymatic reactions. These sensors show promise that they can be incorporated into micro total analysis system (μ-TAS) or "Lab on a Chip".

In summary, a micro DNA sensor was fabricated that can detect enzymatic reaction amperometrically and was characterized by using cyclic voltammetry with ferrocene and POD to demonstrate the capability of conducting electrochemical detection without a conventional Ag/AgCl electrode. Noise reduction was accomplished by surface modification and introducing blocking protein. The structural design of a well in the working electrode and surface treatment on silicon substrate enable reagent confinement over the working electrode. The reagent-electrode contact can be controlled to reduce non-specific binding, not possible with a conventional beaker setup. Urine sample testing shows this DNA sensor is suitable for clinical diagnosis with a short detection time and smaller system size.

A MEMS Based Amperometric Detector for E. Coli Bacteria Using Self-Assembled Monolayers A system is developed for amperometric detection of Escherichia coli (E. coli) based on the integration of microelectromechanical systems (MEMS), self-assembled monolayers (SAMS), DNA hybridization, and enzyme amplification. Using MEMS technology, a detector array was fabricated which has multiple electrodes deposited on a Si wafer and was fully reusable. Using SAMs, a monolayer of the protein streptavidin was immobilized on the working electrode (Au) surface to capture rRNA from E. coli. Three different approaches can be used to immobilize streptavidin onto Au, direct adsorption of the protein on bare Au, binding the protein to a biotinylated thiol SAM on Au, and binding the protein to a biotinylated disulfide monolayer on Au. The biotinylated thiol approach yielded the best results. High specificity for E. coli was achieved using ssDNA-rRNA hybridization and high sensitivity was achieved using enzymatic amplification with peroxidase as the enzyme. The analysis protocol can be conducted with solution volumes on the order of a few microliters and completed in 40 minutes. The detection system was capable of detecting 1000 E. coli cells without polymerase chain reaction with high specificity for E. coli vs. the bacteria Bordetella bronchiseptica.

While conventional methods for detecting bacteria usually involve a morphological evaluation of the organisms as well as testing their ability to grow, such methods are very time consuming and are not feasible under field conditions. The need for rapid detection as well as portability has led to the development of systems that couple pathogen recognition with signal transduction. Both optical and electrochemical detection of bacteria have been reported, although electrochemical methods have an advantage in that they are more amenable to miniaturization. Requirements for an ideal detector include high specificity and high sensitivity using a protocol that can be completed in a relatively short time. Moreover, systems that can be miniaturized and automated offer a significant advantage over current technology, especially if detection is needed in the field. In the following, MEMS technology is integrated with biosensing methods to detect E. coli bacteria.

One of the most effective means of achieving high specificity is to detect the bacteria's genetic material (e.g. rRNA, mRNA, denatured DNA). By choosing a single-stranded DNA (ssDNA) probe whose sequence is complementary only to the target bacteria's rRNA or ssDNA, monitoring the hybridization event allows selective sensing of target cells. To maximize sensitivity, coupling the hybridization event with an enzymatic reaction leads to signal amplification, as each substrate-to-product turnover contributes to the overall signal. Bioassays to detect DNA hybridization that are amplified by enzymatic reaction can still be completed within a reasonably short time. Finally, the miniaturization and portability inherent in electrochemical probes make them excellent candidates for incorporation in MEMS devices.

A layer of silicon dioxide ($S_iO_2$, 1000 Å) was deposited on a bare Si wafer (prime grade, p-type <100>, thickness 500-550 μm) and served as a pad layer underneath the silicon nitride ($Si_3N_4$, 1000 ÅA) to release stress and improve adhesion. MEMS arrays were fabricated with working electrodes of 3.6 mm×3.6 mm etched to form wells of 350 μm depth. The nitride wafer was patterned and bulk etched using KOH along [111] and [100] crystal planes, and depth of the well was controlled by KOH etching time and temperature. The 100 μm wide auxiliary and reference electrodes are separated from their corresponding working electrode by 200 μm. The nitride and oxide were removed by HF etching to release internal stress, and another oxide layer (5000 Å) was deposited for electrical isolation. Electrodes were patterned by PR5214 photo resist reverse imaging and lift-off process with e-beam deposition of Au(2000 Å)/Cr(200 Å). Finally the wafer was bathed in hexamethyldisilazane (HMDS) vapor for three minutes after ten minutes of a 150° C. hot bake to generate a hydrophobic surface on the surrounding Si areas. The hydrophobic nature of the surrounding area along with the 3-dimensional nature of the working electrode allows containment of a liquid droplet in the working electrode. This design effectively minimized non-specific binding of biomolecules to other areas of the MEMS array.

Three different methods were used to deposit streptavidin monolayers on Au: 1) directly adsorbing streptavidin on bare Au, 2) depositing a SAM of a biotinylated thiol, biotin-DAD-C12-SH, and subsequently binding streptavidin, 3) depositing a SAM of a biotinylated disulfide, biotin-HPDP, and subsequently binding streptavidin. In all cases, the Au surfaces were cleaned with concentrated "Piranha" solution (70 vol % $H_2SO_4$, 30 vol % $H_2O_2$) and thoroughly rinsed with deionized water. For depositing streptavidin on bare Au, a solution of 1.0 mg/ml streptavidin (Sigma Chemical Co., S0677) in 0.02M Na phosphate buffer, 0.15M NaCl, pH 7.2, was placed on the surface, allowed to stand for 10 minutes, and rinsed with deionized water. For depositing a SAM of biotin-DAD-C12-SH (12-mercapto(8-biotinamide-3,6-dioxaoctyl)dodecanamide, Roche GmBH, Germany), the procedure of Spinke, et al. (1993) was used wherein samples were incubated for ~18 hours in a 50 μM solution of biotin-DAD-C12-SH in ethanol with $4.5×10^{-4}$M 11-mercapto-1-undecanol (Aldrich Chemical Co., 44,752-8) and rinsed with ethanol and water. The biotin-coated Au surfaces were then exposed to a 1.0 mg/ml streptavidin solution for ~10 minutes and rinsed again with water. For depositing a SAM of biotin-HPDP, (N-[6-(biotinamido)hexyl]-3'-(2'-pyridyldithio)propionamide, Pierce Inc., 21341) samples were incubated for ~18 hours in a 50 μM biotin-HPDP solution in ethanol (with or without $4.5×10^{-4}$M mercaptopropanol) and rinsed with ethanol and water. The surfaces were then exposed to a 1.0 mg/ml streptavidin solution for ~10 minutes and rinsed again with water.

The assay protocol was conducted as follows: 1) 50 μl of lysis reagent (Andcare Inc., 4002-11) was added to a 250 μl sample of bacteria in culture media and incubated for 5 min. at room temperature, 2) 100 μl of probe solution (Andcare Inc., 4002-13) was then added and the mixture was incubated for 10 min. at 65° C., 3) 5 μl of the lysed E. coli/probe solution mixture was placed on the streptavidin coated working electrode of the MEMS detector array and incubated for 10 min. at room temperature, 4) the MEMS detector array was washed with biotin wash solution (Kirkegaard and Perry Laboratories, 50-63-06), 5) 5 μl of Anti-F1-POD (Anti-fluorescein peroxidase, 150 U, Roche Inc., 1 426 346), diluted to 0.75 U/ml or 0.15 U/ml with diluant (Andcare Inc., 4002-14) was placed on the working electrode and incubated for 10 minutes at room temperature, 6) the MEMS array chip was washed again with wash solution, 7) 10 μl of K-blue substrate (Neogen Corp., 300176) was placed on the detector array in such a way that all three electrodes (working, auxiliary, reference) were covered by the substrate solution, and 8) electrochemical measurements were immediately taken. The entire protocol was completed within 40 minutes. Amperometric current vs. time was measured using a CH Instruments 660A electrochemical workstation with picoamp booster and faraday cage. Samples on the MEMS detector array were measured sequentially. The voltage was fixed at −0.1V (vs.

reference), and the cathodic current at 20 seconds was taken as the amperometric signal. At 20 seconds, current values reached steady-state. Cell concentration (cell number) was determined using serial dilutions and culture plate counting.

The performance of the detector depends heavily on the properties of the immobilized streptavidin monolayer. Surface plasmon resonance (SPR, Biacore X system, Biacore, Inc.) and atomic force microscopy (AFM) to characterize the monolayers is performed. For SPR studies of streptavidin binding to bare Au, bare Au chips (J1 sensor chips) were used. For studies of streptavidin binding to biotin-DAD-C-12-SH/Au or biotin-HPDP/Au, the biotin SAM was deposited on the bare Au chips as previously described before the SPR experiments. For best results, new chips were cleaned with diluted $H_2SO_4/H_2O_2$ solution for ~2 min. before performing SPR with bare Au or depositing the biotin SAM. In all cases, 1.0 mg/ml streptavidin in 0.02M Na phosphate, 0.15 M NaCl, pH 7.2 buffer was used. In adsorption experiments with streptavidin on bare Au, flow rates ranged from 1 to 5 µl/min. In the experiments with streptavidin and biotin-DAD-C12-SH/Au, flow rates ranged from 10 to 25 µl/min. In experiments with streptavidin and biotin-HPDP/Au, flow rates ranged from 5 to 10 µl/min. In the desorption experiments, 25 µl of the following solutions were flowed sequentially through the channels at 25 µl/min (total exposure time of 1 min.): 1.0M KCl, 8M urea, 0.5% SDS, 0.1M HCl, 0.1M NaOH, and 40 vol % formamide.

AFM (AutoProbe CP, Thermomicroscopes, Inc.) was performed in the contact mode using ultralever tips with a force of 5.0 nN. To ensure a flat Au surface, the method of Wagner, et al. (1995) was used wherein Au was first deposited via e-beam evaporation on mica and then transferred to Si. In this case, the mica was cleaved to cleanly remove it from the Au without the use of solvent.

On the MEMS detector array, sixteen working electrodes with their corresponding auxiliary and reference electrodes were patterned in a 2.8 cm×2.8 cm area. The detector array was fully reusable as the surface can be cleaned using $H_2SO_4/H_2O_2$ solutions. The same MEMS detector array is reused multiple times by appropriately cleaning the surface and redepositing the SAMs on the working electrode.

Figure 40:
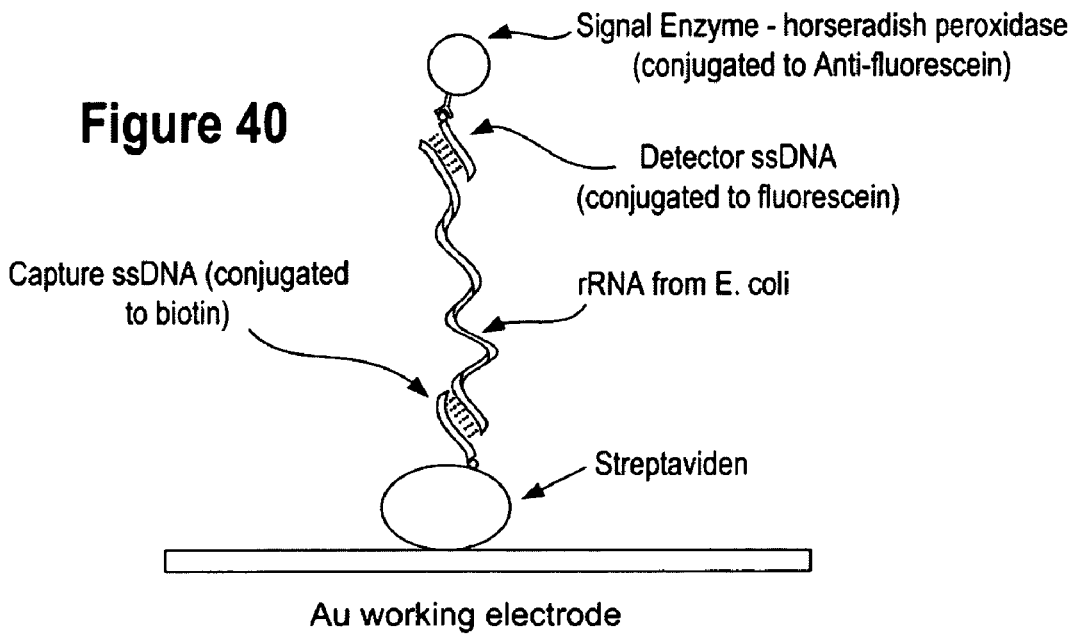
FIG. 40 is a schematic illustrating the electrode surface.

*E. coli* detection is based on DNA hybridization followed by enzymatic reaction. A schematic illustrating the electrode surface is shown in FIG. 40. A streptavidin monolayer is immobilized on the Au working electrode surface to capture the rRNA from *E. coli*. Two ssDNA segments are used in this system. The capture ssDNA, which is conjugated to biotin for streptavidin binding, hybridizes to one end of the *E. coli* rRNA. The detector ssDNA, which is conjugated to fluorescein for binding to anti-fluorescein linked to the enzyme peroxidase (POD), hybridizes to the other end of the *E. coli* rRNA. The capture and detector ssDNA recognize two distinct conservative sequences, and therefore, the hybrid forms only with the specific gene segment from *E. coli*. The oligonucleic hybrid is immobilized through biotin-streptavidin binding onto the Au working electrode and unbound components are washed away. Streptavidin binds biotin with unusually high affinity ($K_d \sim 10^{-15}$M) (Weber, et. al., 1989). After loading the POD onto the hybrid (through Anti-F1-fluorescein binding), substrate is added and enzymatic reaction is detected amperometrically. The substrate solution contains both the substrate $H_2O_2$ and a mediator, 3,3',5,5' tetramethylbenzidine (TMB).

Three different approaches are used to immobilize a streptavidin monolayer on the electrode surface. In the first approach, a streptavidin monolayer was deposited on bare Au via protein adsorption. In the second approach, a SAM of biotin was deposited on the Au using a biotinylated thiol and streptavidin was subsequently bound to the biotin. In the third approach, a SAM of biotin was deposited on the Au using a biotinylated disulfide and streptavidin was subsequently bound to the biotin.

The streptavidin monolayers were characterized using both surface plasmon resonance (SPR) and atomic force microscopy (AFM). SPR has been demonstrated to be a viable technique for monitoring interactions of molecules with metallic (Au, Ag) thin films at the solution-metal interface. This technique can be used to estimate the thickness of a deposited layer as well as to measure the kinetics of association and dissociation SPR is perforemd to monitor deposition of streptavidin on Au using all three approaches. Based on calibrations by the manufacturer (Biacore), 1000 resonance units (RU) in the SPR signal is equivalent to a change of ~1 ng/mm$^2$ in surface protein concentration. Streptavidin has dimensions of ~55×45×50 Å. A full monolayer of streptavidin has an expected density of ~2.8 ng/mm$^2$, calculated based on a 2-dimensional crystalline monolayer. Essentially, a complete monolayer of streptavidin was deposited on the biotinylated thiol SAM/Au (~3000 RU), ~80% "coverage" was obtained with streptavidin deposited on bare Au (~2400 RU), and ~52% "coverage" was obtained with streptavidin deposited on the biotinylated disulfide SAM/Au (~1550 RU). For the biotinylated disulfide, the presence of mercaptopropanol in the solution had a negligible effect on surface coverage as SPR signal increased only ~10% (~1700 RU, data not shown). In all cases, additional protein deposition upon a second injection of protein solution was minimal. Moreover, flow rates had negligible effects on the rate or amount of protein deposited. The SPR results indicate that in all three approaches, only a monolayer of streptavidin, and not multilayers, was deposited on the Au. Finally, these results establish that most of the streptavidin-biotin binding and streptavidin adsorption on bare Au occurs within seconds and can be completed on the order of minutes.

Figure 41:
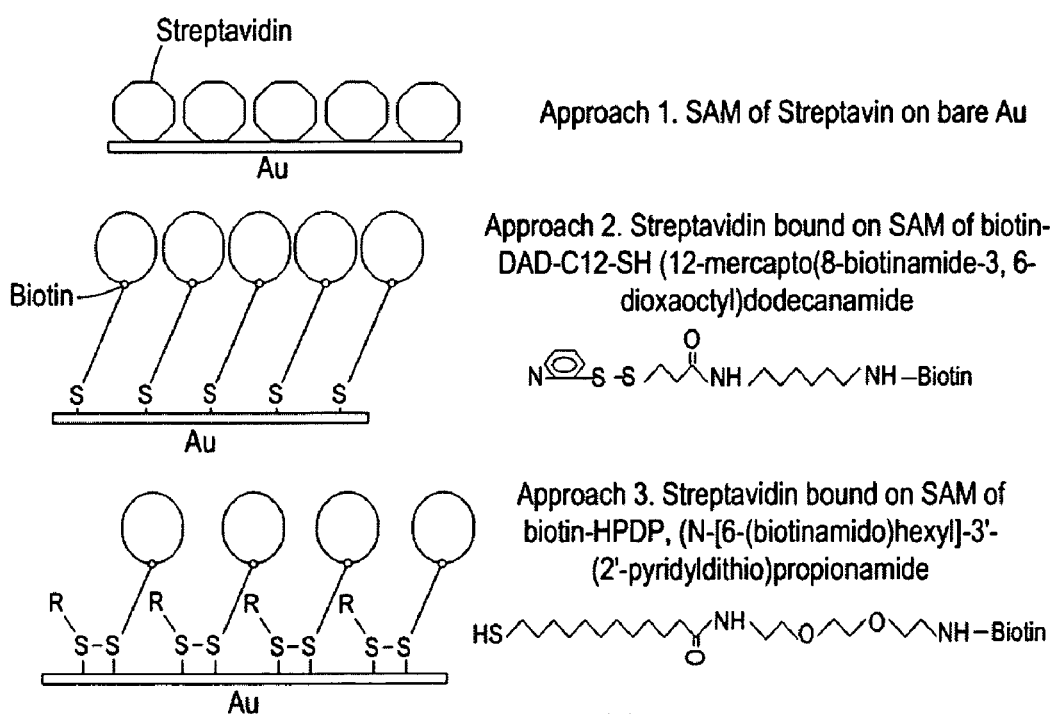
FIG. 41 is a table listing the loss in SPR signal (RU) after treatment with various reagents that are known to dissociate protein-ligand binding and/or denature proteins

Experiments are performed to determine whether streptavidin can be desorbed, i.e. whether streptavidin can be dissociated from the bare Au or from binding to biotin to regenerate the surface. FIG. 41 lists the loss in SPR signal (RU) after treatment with various reagents that are known to dissociate protein-ligand binding and/or denature proteins. As seen in FIG. 41, only 8M urea, 0.5% SDS, and 0.1M NaOH were somewhat effective in desorbing streptavidin from the surface. 1.0M KCl, 0.1M HCl, and 40% formamide were not effective. Streptavidin could not be completely desorbed by any of the reagents, and some protein remained after subjecting the surface to all reagents. These results show that streptavidin had rather good binding to both the biotin SAM as well as to bare Au and that the streptavidin monolayers were relatively stable.

The use of AFM enables us to further characterize the surface by imaging streptavidin directly adsorbed on bare Au. Bare Au had topographic features <10 Å, whereas protein islands on a "partial" monolayer was ~45 Å, consistent with the dimensions of streptavidin. The AFM results confirm the SPR findings that only one monolayer was deposited on the Au. AFM in the contact mode for a "full" protein monolayer showed a featureless surface with evidence of protein dragging (data not shown), and therefore, did not provide any additional information as to surface coverage. Monolayer deposition is also obtained when using biotinylated SAMs and subsequently binding streptavidin.

In the MEMS detector array, a three-electrode system is used with Au for all three electrodes, i.e. working, auxiliary, and reference electrodes. Typically, Ag/AgCl or saturated calomel electrode (SCE) is used as the reference electrode so that reversible oxidation/reduction at fixed potential occurs at the reference electrode. In the MEMS detector array, however, Au is used as the reference electrode to simplify fabrication and to permit a fully reusable array. Maintaining a constant potential is made possible by the use of a 3-electrode system (vs. a 2-electrode system). In this particular application where the reduction of TMB was monitored, Au can be successfully used as the reference electrode because a low voltage difference (−0.1V) was maintained for short periods of time (<1 min).

The Au/Au/Au electrode system is characterized for electrochemical detection by two separate experiments. In the first experiment, a ferrocene film was placed on the electrodes and cyclic voltammetry was conducted to monitor the redox reactions. Cyclic voltammetry for a classic reversible one electron transfer is characterized by a peak separation of ~57 mV between the anodic and cathodic peaks, the same peak currents at peak maximum, and a linear relationship between peak current vs. [scan rate]$^{1/2}$ (Hall, 1991). In the voltammograms obtained with ferrocene at different scan rates, classical redox behavior was observed and a plot of the peak current vs. [scan rate]$^{1/2}$ is linear.

In a second experiment with the Au/Au/Au electrode system, cyclic voltammetry was conducted on the substrate solution only ($H_2O_2$+TMB) and then again on the same solution with POD enzyme. Cycling between −0.2V to +0.50V at a scan rate of 10 mV/s, the substrate solution showed the two electron redox behavior of TMB. The addition of POD to the substrate solution resulted in an increase in the reduction current. A constant potential of −0.10V (vs. reference) was then selected for measurement of POD enzymatic activity. At this potential, the current background was near zero and no substrate oxidation occurred. This potential was optimum for enzymatic activity determination in which a small amount of product (oxidized TMB) was to be measured in the presence of high concentrations of substrate.

For the amperometric detection of *E. coli* rRNA, the performance of the three different streptavidin monolayer surfaces is evaluated. Streptavidin was immobilized on the Au using the three different approaches previously described, and the assay protocol was conducted for the bacteria *E. coli* and *Bordetella bronchiseptica* (*Bordetella*). Since the ssDNA probes are specific for *E. coli*, the *Bordetella* bacteria served as the negative control sample. The purpose of this experiment was to compare the efficacy of the immobilized streptavidin to capture the biotin-rRNA-POD hybrid. Two concentrations of *E. coli* were used, with one sample having ten times the concentration of the other. Moreover, the signal from the *Bordetella* indicates the level of non-specific binding or the achievable "baseline". Results from this experiment are shown in FIG. 42. Since the same bacterial solutions (*E. coli* or *Bordetella*) were used, a direct comparison can be made of the different surfaces. As seen in FIG. 42, streptavidin immobilized via the biotinylated thiol to Au was the best condition for *E. coli* detection. Using the biotin-thiol SAM, good signals for the *E. coli* are obtained while achieving a low baseline signal from the *Bordetella*. For streptavidin immobilized via the biotin-disulfide to Au, current signals for the *E. coli* (both concentrations) were significantly lower, while the baseline was the same as that for the biotin-thiol/streptavidin. In the case of streptavidin directly adsorbed to Au, the signal from the *Bordetella* was much higher, indicating a higher level of non-specific binding of POD to the surface.

Figure 44:
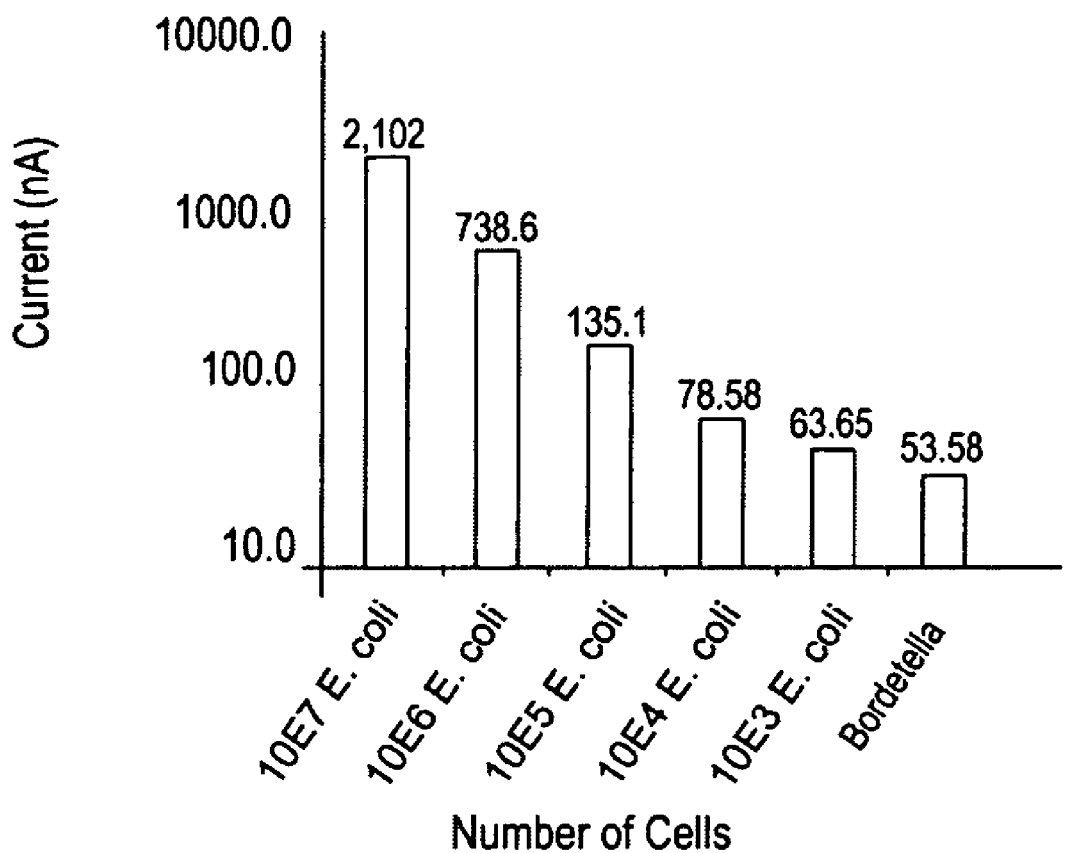
FIG. 44 is a graph showing better discrimination in signals at lower *E. coli* cell numbers by lowering the POD concentration in the assay protocol.

After ascertaining Au/biotin-SH/streptavidin to be the optimal streptavidin surface, the protocol using *E. coli* and *Bordetella* is repeated to determine the sensitivity of the system. Streptavidin is immobilized via the biotin-SH SAM and performed the assay on a series of *E. coli* dilutions along with *Bordetella* as the negative control. Results are shown in FIG. 43. The data indicates that as few as 1000 *E. coli* cells can be detected using the MEMS system. As expected, current signal increased as a function of increasing number of *E. coli* cells in the sample solution. Moreover, by lowering the POD concentration used in the assay protocol (from 0.75 U/ml to 0.15 U/ml), better discrimination can be achieved in signals at lower *E. coli* cell numbers (FIG. 44). As seen in FIG. 44, the current signal for 1000 *E. coli* cells was more than twice that for $2.5 \times 10^5$ *Bordetella* cells. The results using the MEMS system confirm that *E. coli* bacteria was successfully detected using amperometry and SAMs to capture the bacteria rRNA.

The results show that combining MEMS technology with SAMs, DNA hybridization, and enzymatic amperometry leads to a highly specific and sensitive electrochemical detector for bacteria such as *E. coli*. The contribution from each component is critical to the overall success of the system. MEMS technology enables an array of multiple three-electrode "cells" to be deposited on a Si wafer, and the MEMS detector array described is fully reusable as the SAMs can be removed and the Au surfaces regenerated with appropriate cleaning. Moreover, with micromachined channels, valves, pumps and integrated electronics, one can fully automate the sample preparation and assay protocol.

SAMs provide an effective means of functionalizing the Au working electrode to immobilize capture biomolecules, for example, streptavidin. DNA hybridization permits high specificity for pathogenic bacteria as the sequence of the ssDNA probes can be carefully selected to complement only the target. Coupling the hybridization event with an enzymatic reaction provides signal amplification and enhances the sensitivity. Finally, by using electrochemical transduction, a miniaturized portable system with minimum power consumption can be developed.

Rapid detection and a portable instrument is desirable for pathogen sensing. Detection can be achieved within ~40 minutes using this system. Due to the small dimensions and small sample volumes, it is possible to further reduce the assay time by reducing the incubation times (10 minutes) currently used for DNA hybridization and enzyme binding. A distinct advantage of MEMS is the ability to use very small volumes (a few μl) and electrode surface areas (currently 0.13 cm$^2$ for the working electrode, <0.02 cm$^2$ for the auxiliary and reference electrodes). The results show that as few as ~10$^3$ cells can be detected using this system without polymerase chain reaction (PCR). Due to the small volumes and working electrode surface area in the MEMS system, reporting the detection limit in terms of absolute cell numbers is more appropriate than reporting the detection limit in terms of cell concentration (cells/ml). Detection limits on the order of 10$^2$ to 10$^3$ cells/ml have been reported, however, sample volumes of ~1.0 ml with working electrode surface areas ~1 cm$^2$ were typically used. In amperometric enzyme immunofiltration assays, the signal was more than an order of magnitude less when using a 0.1 ml sample than when using a 1.0 ml sample.

Results from amperometric experiments to detect *E. coli* rRNA have shown that the streptavidin monolayer immobilized via the biotinylated thiol SAM approach yielded the best results. This finding is not surprising as SPR data indicated the highest streptavidin surface density or "coverage" when using the biotinylated thiol. It is likely that a well-ordered self-assembled monolayer is formed only with the biotinylated thiol, leading to highest streptavidin surface density. In the case of the biotinylated disulfide, although attachment of the biotin to the Au surface occurs via the Au-S bond, the additional organic group probably hinders the formation of a densely packed monolayer. Streptavidin immobilized via direct adsorption to Au resulted in significantly higher non-specific binding of the POD enzyme to the working electrode. Protein adsorption to Au has been well known as colloidal Au particles attached to various proteins (e.g. streptavidin, immunoglobulins) are commercially available (Nanoprobes, Inc., Yaphank, N.Y.). Streptavidin does not contain cysteine or methionine residues and therefore, does not attach to Au via an Au—S bond. Protein adsorption to Au can occur via interaction of carboxylate groups with Au and is the likely mechanism for streptavidin-Au attachment. Although a streptavidin monolayer can be attached to Au via direct adsorption, whether self-assembly or molecular ordering occurs is questionable. SPR desorption experiments showed the streptavidin-Au attachment to be as robust as streptavidin-biotin binding, i.e. the amount of streptavidin removed due to urea, SDS, and NaOH were similar for streptavidin directly adsorbed on Au as compared to streptavidin attached to biotin. When conducting the assay protocol for E. coli, however, sample solutions contained oligonucleotides as well as cell debris from the lysed E. coli. The data suggests that the presence of other proteins and biomolecules accelerated the desorption of streptavidin from Au, leading to increased non-specific binding of the enzyme POD to the surface.

In summary, E. coli bacteria were successfully detected by incorporating MEMS with SAMs, DNA hybridization, and enzyme amplification. A MEMS-based detection system is demonstrated that is specific for E. coli and capable of detecting 1000 cells without PCR. The process time can be 40 minutes or less. Moreover, the assay can be conducted with solution volumes on the order of a few microliters. The integration of SAMs, DNA hybridization, and enzyme amplification methodologies with MEMS technology makes possible a new generation of devices for pathogenic detection.

While this invention has been described with reference to illustrative embodiments, this description is not intended to be construed in a limiting sense. Various modifications of the illustrative embodiments, as well as other embodiments of the invention, which are apparent to persons skilled in the art to which the invention pertains are deemed to lie within the spirit and scope of the invention.

The invention claimed is:

1. A method of detecting the presence or measuring the quantity of a target analyte in a sample, comprising:

positioning the sample on a sensor, the sensor including a working electrode, a reference electrode and a counter electrode on a substrate, the reference electrode consisting of a single layer of an electrically conductive material and a self-assembly monolayer, the self-assembly monolayer being bonded to the layer of electrically conductive material and including biotinylated thiol molecules that include a sulfur bonded directly to the layer of electrically conductive material;

conducting an analysis of the sample that includes controlling a potential difference between the reference electrode and the working electrode while measuring a current flowing through the working electrode, wherein the potential is controlled so as to cause a redox reaction between a component in the sample and the working electrode, and the current through the working electrode is balanced by a current through the counter electrode; and employing the measured current to determine the presence or quantity of a target analyte in the sample.

2. The method of claim 1, wherein the sensor includes an adhesive underneath each of the electrodes, the adhesive allowing for better adhesion of each of the electrodes to the substrate.

3. The method of claim 1, wherein the sample is a biological fluid containing macromolecules.

4. The method of claim 1, wherein the sample is a biological fluid containing ionic molecules or atoms.

5. The method of claim 1, wherein the substrate is selected from the group consisting of silicon, gallium arsenide, plastic and glass.

6. The method of claim 1, wherein the substrate comprises a material made out of silicon.

7. The method of claim 1, wherein the electrically conductive material is selected from the group consisting of gold, aluminum, chromium, copper, platinum, titanium, nickel and titanium.

8. The method of claim 1, wherein the electrically conductive material is gold.

9. The method of claim 2, wherein the adhesive is selected from the group of consisting of chromium, titanium, and glue.

10. The method of claim 2, wherein the adhesive includes chromium.

11. The method of claim 1, wherein the substrate further includes a well structure containing at least one of the electrodes.

12. The method of claim 1, wherein each of the electrically conductive electrodes consists of a single layer of gold.

13. The method of claim 1, further comprising: calibrating the sensor with a first calibrating solution that contains a known amount of a target analyte to be detected and a second calibrating solution that contains an undetectable amount of the target analyte to be detected.

14. The method of claim 1, wherein a surface on at least one of the electrodes is modified for anchoring molecules on the surface.

15. The method of claim 1, wherein the electrodes are in contact with the substrate.

16. The method of claim 1, wherein the electrically conductive material associated with each electrode extends from each electrode to an electrical pad positioned on the substrate.

17. The method of claim 1, wherein each of the electrodes is constructed of the same material.

18. The method of claim 9, wherein the reference electrode and the counter electrode each have a shape that is different from a shape of the working electrode.

19. The method of claim 1, wherein the sample is a liquid.

20. The method of claim 1, wherein positioning the sample on the sensor includes forming a drop of the sample over the electrodes.

21. The method of claim 1, wherein the potential difference between the working electrode and the reference electrode is controlled by application of a current through the counter electrode.

22. The method of claim 1, wherein the sensor consists of the working electrode, counter electrode and reference electrode positioned on the substrate.

23. The method of claim 1, wherein the sensor occupies an area of 160 μm$^2$ to 25 mm$^2$.

24. The method of claim 1, wherein the analysis is a cyclic voltammetry analysis.

25. The method of claim 1, wherein the analysis is an amperometric analysis.

26. The method of claim 1, wherein controlling the potential difference between the working electrode and the reference electrode includes sweeping the potential difference between the working electrode and the reference electrode across a range of values.

27. The method of claim 1, wherein the analysis includes measuring the current between the counter electrode and the working electrode while sweeping the potential difference between the working electrode and the reference electrode across a range of values.

28. The method of claim 1, wherein the reference electrode, the working electrode and the counter electrode each consist of a single layer of an electrically conducting material.

29. The method of claim 1, wherein the self-assembly monolayer is positioned on the working electrode.

30. The method of claim 1, wherein the reference electrode is arranged about the perimeter of the working electrode such that a portion of the working electrode is positioned between different regions of the reference electrode.

31. The method of claim 1, wherein the counter electrode is arranged about the perimeter of the working electrode such that a portion of the working electrode is positioned between different regions of the reference electrode.

32. The method of claim 1, wherein employing the measured current to determine the presence or quantity of a target analyte in the sample includes employing the potential in combination with the measured current to determine the presence or quantity of the target analyte in the sample.

33. The method of claim 1, further comprising:
forming the self-assembly monolayer on at least one of the electrodes before positioning the sample on the sensor.

34. The method of claim 29, further comprising:
forming the self-assembly monolayer on the working electrode before positioning the sample on the sensor.

35. The method of claim 1, wherein the self-assembly monolayer is positioned on the working electrode, and the counter electrode, the self-assembly monolayer including biotinylated thiol molecules bonded to the counter electrode and the working electrode.

36. The method of claim 35, further comprising:
forming the self-assembly monolayer on the working electrode, the counter electrode, and the reference electrode before positioning the sample on the sensor.

37. The method of claim 35, wherein a portion of the biotinylated thiol molecules include a sulfur that is bonded directly to the working electrode and another portion of the biotinylated thiol molecules include a sulfur that is bonded directly to the counter electrode.

38. The method of claim 1, wherein the self-assembly monolayer is positioned on at least the reference electrode, the self-assembly monolayer including biotinylated thiol molecules bonded to at least the reference electrode.

39. The method of claim 1, wherein the self-assembly monolayer is positioned on the working electrode, the self-assembly monolayer including biotinylated thiol molecules bonded to the working electrode.

* * * * *